US008604082B2

(12) United States Patent
Singh

(10) Patent No.: US 8,604,082 B2
(45) Date of Patent: *Dec. 10, 2013

(54) METHOD TO TREAT PREMATURE EJACULATION IN HUMANS

(75) Inventor: Chandra U. Singh, San Antonio, TX (US)

(73) Assignee: Trinity Laboratories, Inc., San Antonio, TX (US)

( * ) Notice: Subject to any disclaimer, the term of this patent is extended or adjusted under 35 U.S.C. 154(b) by 946 days.

This patent is subject to a terminal disclaimer.

(21) Appl. No.: 12/097,157

(22) PCT Filed: Dec. 11, 2006

(86) PCT No.: PCT/US2006/061873
§ 371 (c)(1), (2), (4) Date: Nov. 26, 2008

(87) PCT Pub. No.: WO2007/070779
PCT Pub. Date: Jun. 21, 2007

(65) Prior Publication Data
US 2009/0215810 A1  Aug. 27, 2009

Related U.S. Application Data

(60) Provisional application No. 60/749,813, filed on Dec. 13, 2005.

(51) Int. Cl.
  *A01N 37/10* (2006.01)
  *A01N 43/54* (2006.01)
  *A01N 43/42* (2006.01)
  *A01N 43/38* (2006.01)
  *A01N 37/36* (2006.01)
  *C07D 239/42* (2006.01)

(52) U.S. Cl.
  USPC ...... 514/569; 514/256; 514/210.21; 514/410; 514/289; 514/159

(58) Field of Classification Search
  USPC .............................. 514/569, 256, 210.21, 289
  See application file for complete search history.

(56) References Cited

U.S. PATENT DOCUMENTS

| 3,710,795 | A |   | 1/1973  | Higuchi et al. | 128/260 |
|-----------|---|---|---------|----------------|---------|
| 4,507,323 | A |   | 3/1985  | Stern et al.   | 514/649 |
| 4,940,731 | A |   | 7/1990  | Bick et al.    | 514/657 |
| 5,059,603 | A | * | 10/1991 | Rubin          | 514/263.31 |
| 5,063,915 | A |   | 11/1991 | Wyckoff        | 128/79  |
| 5,151,448 | A |   | 9/1992  | Crenshaw       | 514/651 |
| 5,276,042 | A |   | 1/1994  | Crenshaw et al.| 514/321 |
| 5,327,910 | A |   | 7/1994  | Flynn          | 128/842 |
| 5,468,212 | A |   | 11/1995 | Shooter        | 600/39  |
| 5,535,758 | A |   | 7/1996  | Hagihara       | 128/897 |
| 5,707,999 | A |   | 1/1998  | Cavallini      | 514/260 |
| 5,919,826 | A | * | 7/1999  | Caruso         | 514/629 |
| 6,037,360 | A |   | 3/2000  | Smith et al.   | 514/397 |
| 6,403,597 | B1 |  | 6/2002  | Wilson         | 514/256 |
| RE38,115  | E  |  | 5/2003  | Smith et al.   | 514/289 |
| 6,794,387 | B2 |  | 9/2004  | Allerton et al.| 514/243 |
| 6,974,839 | B2 |  | 12/2005 | Bar-Or         | 514/647 |
| 7,645,767 | B2 |  | 1/2010  | Singh et al.   |         |
| 2004/0235954 | A1 | | 11/2004 | Singh         | 514/569 |
| 2005/0113294 | A1 | | 5/2005  | Dolle         | 514/9   |
| 2010/0120780 | A1 | | 5/2010  | Singh         |         |
| 2011/0039875 | A1 | | 2/2011  | Singh         |         |

FOREIGN PATENT DOCUMENTS

| WO | WO 95/13072    | 5/1995  |
|----|----------------|---------|
| WO | WO 96/32952    | 10/1996 |
| WO | WO 2005/102338 | 11/2005 |
| WO | 2006/053012 A2 | 5/2006  |
| WO | WO 2007/070779 | 4/2007  |

OTHER PUBLICATIONS

International Search Report issued in European Application No. 06846555.8-2403, dated Nov. 19, 2008.
Balon, "Intermittent amantadine for fluoxetine-induced anorgasmia," *Journal of Sex and Marital Therapy*, 22:290-292, 1996.
Chen et al., "Isobolographic analysis of the analgesic interactions between ketamine and tramadol," *J. Pharm. Pharmacol.*, 54:623-631, 2002.
Richardson et al., "A review of controlled trials in the pharmacological treatment of premature ejaculation," *International Journal of STD & AIDS*, 16:651-658, 2005.
Samer et al., "Genetic polymorphism and drug interactions: their importance in the treatment of pain," *Can. J. Anesth.*, 52:806-821, 2005, English Abstract.
Ünlügenc et al., "A comparative study on the analgesic effect of tramadol, tramadol plus magnesium, and tramadol plus ketamine for postoperative pain management after major abdominal surgery," *Acta. Anaesthesiologica Scand.*, 46:1025-1030, 2002.
Zhang et al., "Comparison between sildenafil plus setraline and sertraline alone in the treatment of premature ejaculation," *National Journal of Andrology*, 11:520-522, 2005, English Abstract.
Albers et al., "Safety and tolerance of oral dextromethorphan in patients at risk for brain ischemia," *Stroke*, 22:1075-1077, 1991.
Applebaum et al., "Dextromethorphan in the treatment of ALS: a pilot study," *Neurology*, 41 (Suppl. 1): 393 (Abstract # 960S), 1991.
Balon, "Antidepressants in the treatment of premature ejaculation," *Journal of Sex & Marital Therapy*, 22:85-96, 1996.
Barnung et al., "Respiratory depression following oral tramadol in a patient with impaired renal function," *Pain*, 71:111-112, 1997.
Boolell et al., "Sildenafil: an orally active type 5 cyclic GMP-specific phosphodiesterase inhibitor for the treatment of penile erectile dysfunction," *Int. J. Impot. Res.*, 8:47-52, 1996.

(Continued)

*Primary Examiner* — Shirley V Gembeh
(74) *Attorney, Agent, or Firm* — Nevrivy Patent Law Group P.L.L.C.

(57) ABSTRACT

The present invention belongs to the fields of pharmacology, medicine and medicinal chemistry, and provides methods and compositions for treating sexual dysfunction; more particularly, the invention relates to treatment of premature ejaculation in humans.

15 Claims, 3 Drawing Sheets

(56) References Cited

OTHER PUBLICATIONS

Broly et al., "Effect of quinidine on the dextromethorphan O-demethylase activity of microsomal fractions from human liver," *Br. J. Clin. Pharmacol.*, 28:29-36, 1989.

Broly et al., "Inhibitory studies of mexiletine and dextromethorphan oxidation in human liver microsomes," *Biochem. Pharmacol.*, 39:1045-1053, 1990.

Burnett, "Role of nitric oxide in the physiology of erection," *Biol. Reprod.*, 52:485-9, 1995.

Carpenter et al., "Dextromethorphan and dextrorphan as calcium channel antagonists," *Brain Research*, 439:372-375, 1988.

Cavallini, "Alpha-1 blockade pharmacotherapy in primitive psychogenic premature ejaculation resistant to psychotherapy," *Eur. Urology*, 28:126-130, 1995.

Chan et al., "Mechanism-based inactivation of human cytochrome P450 3A4 by grapefruit juice and red wine," *Life Sciences*, 62:PL135-142, 1998.

Choi, "Dextrorphan and dextromethorphan attenuate glutamate neurotoxicity," *Brain Res.*, 403:333-336, 1987.

Craviso and Musacchio, "High-affinity dextromethorphan binding sites in guinea pig brain. II. Competition experiments," *Mol. Pharmacol.*, 23:629-640, 1983.

Daly and Fredholm, "Caffeine—an atypical drug of dependence," *Drug Alcohol Depend.*, 51:199-206, 1998.

Dayer et al., "[Pharmacology of tramadol]," *Drugs*, 53(Suppl. 2):18-24, 1997.

Ferrari and Giuliani, "The selective D2 dopamine receptor antagonist eticlopride counteracts the ejaculatio praecox induced by the selective D2 dopamine agonist SND 919 in the rat," *Life Sciences*, 55:1155-1162, 1994.

Fredholm et al., "Actions of caffeine in the brain with special reference to factors that contribute to its widespread use," *Pharmacol. Rev.*, 51:83-133, 1999.

Fukuda et al., "Grapefruit component interacting with rat and human P450 CYP3A: possible involvement of non-flavonoid components in drug interaction," *Biol. Pharm. Bull.*, 20:560-564, 1997.

Goldstein et al., "Oral sildenafil in the treatment of erectile dysfunction," *The New England Journal of Medicine*, 338:1397-1404, 1998.

Guttendorf et al., "Simplified phenotyping with dextromethorphan by thin-layer chromatography: application to clinical laboratory screening for deficiencies in oxidative drug metabolism," *Ther. Drug Monit.*, 10:490-498, 1988.

Hull et al., "The roles of nitric oxide in sexual function of male rats," *Neuropharmacology*, 33:1499-1504, 1994.

International Preliminary Report on Patentability, issued in Application No. PCT/US2006/061873, dated Dec. 13, 2005.

Jee et al., "The effect of chronic coffee drinking on blood pressure: a meta-analysis of controlled clinical trials," *Hypertension*, 33:647-652, 1999.

Köppel et al., "Urinary metabolism of dextromethorphan in man," *Arzneim.-Forsch./Drug Research*, 37:1304-1306, 1987.

Metz et al., "Premature ejaculation: a psychophysiological review," *Journal of Sex & Marital Therapy*, 23:3-23, 1997.

Obermeier et al., "Effects of bioflavonoids on hepatic P450 activities," *Xenobiotic.*, 25:575-584, 1995.

PCT International Search Report and Written Opinion, issued in Application No. PCT/US06/61873, dated Sep. 26, 2007.

Porter and Coon, "Cytochrome P-450: Multiplicity of isoforms, substrates, and catalytic and regulatory mechanisms," *J. Biol. Chem.*, 266:13469-13472, 1991.

Singh, "A Method to Treat Premature Ejaculation in Humans," U.S. Appl. No. 60/912,760, filed Apr. 19, 2007.

Waldinger et al., "Ejaculation-retarding properties of paroxetine in patients with primary premature ejaculation: a double-blind, randomized, dose-response study," *British Journal of Urology*, 79:592-595, 1997.

Walker and Hunt, "An open label trial of dextromethorphan in Huntington's disease," *Clin. Neuropharmacol.*, 12:322-330, 1989.

Weinbroum et al., "The role of dextromethorphan in pain control," *Can. J. Anesth.*, 47:585-96, 2000.

Claims of copending U.S. Appl. No. 13/877,980.

\* cited by examiner

METHOD TO TREAT PREMATURE EJACULATION IN HUMANS

CROSS-REFERENCE TO RELATED APPLICATIONS

This application is a national phase application under 35 U.S.C. §371 of International Application No. PCT/US2006/061873 filed Dec. 11, 2006, which claims the benefit of U.S. Provisional Application 60/749,813 filed Dec. 13, 2005, the entire disclosures of which are specifically incorporated herein by reference without disclaimer.

BACKGROUND OF THE INVENTION

Primitive premature ejaculation is regarded as the most common sexual disorder of the male. This may cause a loss of the ability to achieve sexual accommodation which is necessary for the satisfaction of the human instinctive desire. Recently, it has been determined that the number of cases manifesting various symptoms caused by such loss of sexual accommodation is rather large. The sexual problems due to premature ejaculation in men lead to social difficulties, such as asthenia due to the loss of self-confidence, as well as domestic discord. Premature ejaculation includes persistent or recurrent ejaculation before, upon, or shortly after penetration.

By nature, a woman is so evolved that she experiences the sex act markedly less intensely than a man, at least at the commencement of sexual activity. She must, therefore, have more time in order to reach the orgasm which provides natural relaxation of the whole nervous system strained to the maximum during the act. To this day the sense of touch plays an important role in human sex life; particularly sensitive to touch are the erogenous zones, first and foremost among them being the areas where skin borders on mucous membrane as, for example, in the vicinity of the oral cavity, the rectum, female genitals and breast nipples. The erogenous zone of a woman can be her entire body surface. In such cases it is possible to evoke lascivious feelings in her by touching any part of her body. But it is most often the case that erogenous zones are localized in strictly defined places such as: the clitoris, labia minora and the vagina. There are, additionally, many such sensitive points apart from the sex organs. These are: the lips, the ears, eyelids, neck, nipples, etc. In some cases these points are so sensitive that merely touching them can produce an orgasm in a woman.

However in the case of men, the erogenous zones are confined solely to the genitals and adjacent areas. It is not surprising, therefore, that an experienced male partner is sometimes obliged to undertake veritable journeys of exploration, in his search for these points, without which no one can activate the complex apparatus of female sexual reflexes. That is one reason the male often needs incomparably less time in order to reach orgasm—which usually concludes the sex act not only for himself but also for his partner. At the commencement of the sex act the man already finds himself at a certain level of excitement, which is essential to erection and without which this act becomes quite impossible. He is unable to continue the act out of consideration for his partner because immediately after orgasm and the associated ejaculation detumescence takes place and all further frictions in vagina are impossible.

The ideal intercourse would be one in which, following immersing the penis into the vagina, both parties reached the boundary of orgasm simultaneously and, having crossed it, ended the sex act together (FIG. 1). This happens sometimes where a woman experienced in sexual intercourse can compensate for the excitement missing at the beginning of the act and reach the finishing line together with her partner in spite of that. For young and middle-aged men the norm of normal ejaculation vacillates between 2-6 minutes after the immersing the penis into the vagina.

The premature ejaculation occurs very frequently in the modern human sexual act. It concerns the fact that shortly after immersing the penis into the vagina takes place (FIG. 2), sometimes after 2-3 movements, ejaculation and orgasm occur; the erection vanishes and the sex act is ended. Obviously in such a situation the woman is only aroused, while there can be no question of release. Obviously there can be no question of sexual satisfaction and normal relaxation of the female partner in the presence of any kind of male impotence, whether through inadequate erection or through premature ejaculation.

Erection of the penis may be a self-perpetuating process of three steps: 1) vasodilation; 2) release of endogenous smooth-muscle relaxants; and, 3) progression of these effects distal from the initial site of onset. This has been termed the "cascade effect" (Andersson et al 1995). Papaverine is an opium alkaloid and works as a smooth muscle relaxer possibly by cyclic GMP phosphodiesterase inhibition. It relaxes the musculature of the vascular system of the penis and increases blood flow (Papaverine Topical Gel Treatment For Erectile Dysfunction, Urology, Vol. 133(2) (1995), pp. 361-365). Another compound found useful in the treatment of impotence is prostaglandin E1, a naturally occurring compound that acts to increase arterial inflow to the penis and may also restrict venous outflow. Prostaglandin E1 is preferred to other compounds used in injections for the treatment of impotence because it is metabolized locally in the penis and is less likely to cause systemic symptoms such as hypotension. As a modified vascular tissue, corpora cavernosa of the penis (ccp) produces and secretes the same range of autocrine and paracrine regulators as conventional vascular tissue. The smooth muscle tone of the ccp, however, does not appear to be regulated in the same manner as in the vascular wall. Presently it is postulated that the tone or contractility of ccp is modulated by adrenergic regulation and locally produced NO and endothelin. In the ccp, most studies have been directed to observing the relaxing effects of NO (Rajfer et al 1992; Burnett 1995), vasoactive intestinal peptide (VIP), calcitonin gene-related peptide (CGRP) and parasympathetic innervation, which also have similar effects on conventional and ccp vascular smooth muscle.

During normal penile erections, when the inflow of blood to the ccp engages the sinusoidal spaces, the trabecular tissue compresses small cavernosal veins against the thick fibrous tissue surrounding the corpora to maintain the erection. To mediate these changes in blood flow, nitric oxide is released from postsynaptic parasympathetic neurons and, to a lesser extent, endothelial cells and α-adrenergic neurons are inhibited in the arterial and trabecular smooth muscle. Nitric oxide, which is readily diffusible, stimulates the formation of increased cyclic guanosine monophosphate (GMP) in the corpus cavernosum by guanylate cyclase to relax the smooth muscle cells.

Recently, the oral use of the citrate salt of sildenafil has been approved by the U.S. Food and Drug Administration (FDA) for the treatment of male erectile dysfunction. The composition of matter of sildenafil is first disclosed in the European patent EP 0463756 and there is no composition of matter patent covering sildenafil in the US or other countries besides the European ones. Sildenafil is reported to be a selective inhibitor of cyclic-GMP-specific phosphodiesterase type 5 (PDE5), the predominant isozyme metabolizing cyclic GMP formed in the corpus cavernosum (Boolell et al 1996). Since sildenafil is a potent inhibitor of PDE5 in the corpus cavernosum, it is believed to enhance the effect of nitric oxide, thereby increasing cavernosal blood flow in the penis, especially with sexual stimulation. Inasmuch as sildenafil at the currently recommended doses of 25-100 mg has little effect in the absence of sexual stimulation, sildenafil is believed to restore the natural erectile response to sexual stimulation but not cause erections in the absence of such stimulation (Goldstein 1998). The localized mechanism by which cyclic GMP stimulates relaxation of the smooth muscles has not been elucidated.

Normal ejaculatory function in the human male implies a coordinated sequence of smooth and striate muscular contractions to promote projectile, antegrade transport of seminal fluid. This process begins with transmission of afferent nerve stimuli via the internal pudendal nerve from the penile shaft to higher centers. To complete the ejaculatory reflex efferent stimuli are transmitted from the anterolateral columns of the spinal cord and emerging from the thoracolumbar level to comprise a hypogastric or sympathetic plexus. From the interior mesenteric ganglion short adrenergic postganglionic fibers terminate in the seminal vesicles, vasal ampullae, and bladder neck. Sympathetic innervation of the seminal vesicles results in seminal emission into the posterior urethra. Appropriately timed bladder neck closure prevents retrograde passage of this semen bolus, which is propelled in the antegrade direction by clonic contracts of the bulbocavernosus and ischiocavernosus muscles of the pelvic floor. Ejaculation is a centrally, integrated peripheral evoked reflex, which occurs as a result of α1-adrenergic receptor activation. Effective pharmacological drugs for the treatment of premature ejaculation exist, but they suffer from severe side effects, for example clomipramine and phenoxybenzamine. Other treatments have a limited effectiveness (metoclopramide and the like).

Dextromethorphan (frequently abbreviated as DM) is the common name for (+)-3-methoxy-N-methylmorphinan (FIG. 3). It widely used as a cough syrup, and is described in references such as Rodd 1960 (full citations to articles are provided below) and Goodman and Gilman's Pharmacological Basis of Therapeutics. Briefly, DM is a non-addictive opioid comprising a dextrorotatory enantiomer (mirror image) of the morphinan ring structure which forms the molecular core of most opiates. DM acts at a class of neuronal receptors known as sigma receptors. These are often referred to as sigma opiate receptors, but there is some question as to whether they are opiate receptors, so many researchers refer to them simply as sigma receptors, or as high-affinity dextromethorphan receptors. They are inhibitory receptors, which means that their activation by DM or other sigma agonists causes the suppression of certain types of nerve signals. Dextromethorphan also acts at another class of receptors known as N-methyl-D-aspartate (NMDA) receptors, which are one type of excitatory amino acid (EAA) receptor. Unlike its agonist activity at sigma receptors, DM acts as an antagonist at NMDA receptors, which means that DM suppresses the transmission of nerve impulses mediated via NMDA receptors. Since NMDA receptors are excitatory receptors, the activity of DM as an NMDA antagonist also leads to the suppression of certain types of nerve signals, which may also be involved in some types of coughing. Due to its activity as an NMDA antagonist, DM and one of its metabolites, dextrorphan, are being actively evaluated as possible treatments for certain types of excitotoxic brain damage caused by ischemia (low blood flow) and hypoxia (inadequate oxygen supply), which are caused by events such as stroke, cardiac arrest, and asphyxia. The anti-excitotoxic activity of dextromethorphan and dextrorphan, and the blockade of NMDA receptors by these drugs, are discussed in items such as Choi 1987, Wong et al 1988, Steinberg et al 1988, and U.S. Pat. No. 4,806,543 (Choi 1989). Dextromethorphan has also been reported to suppress activity at neuronal calcium channels (Carpenter et al 1988). Dextromethorphan and the receptors it interacts with are further discussed in Tortella et al 1989, Leander 1989, Koyuncuoglu & Saydam 1990, Ferkany et al 1988, George et al 1988, Prince & Feeser 1988, Feeser et al 1988, Craviso and Musacchio 1983 and Musacchio et al 1988.

DM disappears fairly rapidly from the bloodstream (see, e.g., Vetticaden et al 1989 and Ramachander et al 1977). DM is converted in the liver to two metabolites called dextrorphan and 3-methoxymorphinan, by an enzymatic process called O-demethylation; in this process, one of the two pendant methyl groups is replaced by hydrogen. If the second methyl group is removed, the resulting metabolite is called 5-hydroxymorphinan. Dextrorphan and 5-hydroxymorphinan are covalently bonded to other compounds in the liver (primarily glucuronic acid or sulfur-containing compounds such as glutathione) to form glucuronide or sulfate conjugates which are eliminated fairly quickly from the body via urine bloodstream. This enzyme is usually referred to as debrisoquin hydroxylase, since it was discovered a number of years ago to carry out a hydroxylation reaction on debrisoquin. It is also referred to in various articles as P450DB or P450-2D6. It apparently is identical to an enzyme called sparteine monooxygenase, which was shown years ago to metabolize sparteine; it was not until recently that scientists realized that a single isozyme appears to be primarily responsible for oxidizing both debrisoquin and sparteine, as well as dextromethorphan and various other substrates. Debrisoquin hydroxylase belongs to a family of enzymes known as "cytochrome P-450" enzymes, or as "cytochrome oxidase" enzymes. Monooxygenation of chemical materials has been ascribed to cytochromes P450 (P450). These hemoprotein containing monooxygenase enzymes displaying a reduced carbon monoxide absorption spectrum maximum near 450 nm have been shown to catalyze a variety of oxidation reactions including hydroxylation of endogenous and exogenous compounds (Jachau, 1990). An extensive amount of research has been conducted on the mechanism's by which P450's can catalyze oxygen transfer reactions (Testa and Jenner, 1981; Guengerich, 1992; Brosen et al, 1990; Murray et al, 1990; and Porter et al, 1991).

The P450 reaction cycle proceeds briefly as follows: initial binding of a substrate molecule (RH) to the ferric form of the cytochrome results in the formation of a binary complex and a shift in the spin equilibrium of the ferric enzyme from the low- to high-spin state. Some evidence has been presented that suggests this configuration more readily accepts an electron from the flavoprotein reductase to form the ferrous P450-substrate complex. However, not all P450s exhibit a relationship between high-spin content and reduction rate. Indeed, it has been proposed that several factors, including the nature of the P450 substrate, the topography of the enzyme/substrate complex, and the potentials of oxidizable atoms each play a role in regulation of the reduction rate. Molecular oxygen binds to the ferrous P450-substrate complex to form the ferrous dioxygen complex which is then reduced by a second electron from the P450 reductase (or perhaps, in some cases, from reduced nicotinamide adenine dinucleotide via cytochrome b5 and its reductase). Dioxygen bond cleavage in the reduced ferrous dioxygen complex results in the insertion of one atom of oxygen into the substrate, reduction of the other oxygen atom to water, and restoration of the ferric hemoprotein.

Individual members of the P450 family of enzymes and associated mixed function oxidase activities have been described in extrahepatic tissues including brain, adrenal, kidney, testis, ovary, lung and skin. Individual P450s have likewise been characterized in terms of their inducibility by selected chemical classes. Induction of specific P450 enzymes, such as the P450 1A1 and 1A2 subfamily have been extensively studied with respect to regulatory processes of increased mRNA transcription and expression of enzymatic activity. It has been ascertained that materials such as beta-naphthaflavone (beta-NF), 3-methylcholanthrene (3-MC), arochlor 1254 (ACLR) and 2,3,7,8-tetrachlorodibenzo-p-dioxin (TCDD) are materials that have been categorized as inducers of P450 enzymes bearing the designated P450 1A subfamily (Murray et al, 1990; and Guengerich, 1989).

A number of compounds inhibit the activity of the debrisoquin hydroxylase (sparteine monooxygenase) isozyme (Inaba et al 1985). The most powerful of these inhibitors is quinidine (FIG. 3), a dextrorotatory stereoisomer of quinine; it is normally used to treat cardiac arrhythmias. Inaba et al (1986) and Nielsen et al (1990) discuss the ability of quinidine to inhibit the oxidation of sparteine in in vivo animal tests, and Brinn et al (1986), Brosen et al (1987), and Broly et al (1989) discuss the ability of quinidine to inhibit DM metabolism in liver cell preparations. In addition to the inhibition of debrisoquin hydroxylase, which is exceptionally potent and easily demonstrated, other cytochrome P450 isozymes are also likely to be suppressed by quinidine, with varying levels of binding affinity. Accordingly, even though quinidine exerts its most marked effect on debrisoquin hydroxylase, it is likely to suppress a number of other cytochrome P450 enzymes as well, thereby subjecting a patient to a more general loss of normal and desirable liver activity. The primary oxidized metabolic product of dextromethorphan is dextrorphan, which is widely believed among neurologists to be active in exactly the same manner as dextromethorphan; both drugs reportedly are sigma agonists, NMDA antagonists, and calcium channel antagonists. It has been shown that the administration of a compound which inhibits debrisoquin hydroxylase, in conjunction with DM, causes a major increase in the concentration and stability of DM in the blood of patients, compared to patients who receive only DM; and the administration of a debrisoquin hydroxylase inhibitor in conjunction with DM has a clear and substantial impact on the detectable effects of DM in humans.

Tramadol has the chemical name (+/−)-trans (RR,SS)-2-[(di-methylamino)methyl]-1-(3-methoxyphenyl) cyclohexanol, and which is often erroneously referred to in literature as the cis(RS,SR) diastereomer. Tramadol is a centrally acting, binary analgesic that is neither opiate-derived, nor is it an NSAID. It is used to control moderate pain in chronic pain settings, such as osteoarthritis and post-operative analgesia, and acute pain, such as dental pain.

Tramadol is a racemate and consists of equal quantities of (+)- and (−)-enantiomers. It is known that the pure enantiomers of tramadol have a differing pharmaceutical profiles and effects when compared to the racemate. The (+)-enantiomer is distinguished by an opiate-like analgesic action due its binding with the μ-opiate receptor, and both enantiomers inhibit 5-hydroxytryptamine (serotonin) and noradrenaline (norepinephrine) reuptake, which is stronger than that of racemic mixtures of tramadol, while distinct inhibition of noradrenaline reuptake is observed with the (−)-enantiomer. It has been proven for (+)- and (−)-tramadol that, depending upon the model, the two enantiomers mutually reinforce and enhance their individual actions (Raffa, R. et al., 1993; Grond S et al, 1995 and Wiebalck A et al., 1998). It is obvious to conclude that the potent analgesic action of tramadol is based on this mutually dependent reinforcement of action of the enantiomers. Tramadol's major active metabolite, O-desmethyltramadol (M1), shows higher affinity for the μ-opiate receptor and has at least twice the analgesic potency of the parent drug. O-desmethyl-N-mono-desmethyltramadol (referred to as M5 in some places in the following text and in the literature) is known as one of the in vivo metabolites of tramadol (1RS,2RS)-2-[(dimethylamino)methyl]-1-(3-methoxyphenyl) cyclohexanol (Lintz et al., 1981). M5 penetrates the blood-brain barrier to only a limited extent, as the effects on the central nervous system, for example analgesic effects, are distinctly less pronounced on intravenous administration than on intracerebroventricular administration.

Despite the fact that tramadol is chemically unrelated to the opiates adverse side effects associated with administration of tramadol are similar to those of the opiates if used at higher doses.

Caffeine is an alkaloid obtained from the leaves and seeds of the *Coffea arabica* or coffee plant and from the leaves of *Thea sinensis* or tea. Caffeine is a methylated xanthine and chemically denoted as 3,7-dihydro-1,3,7-trimethyl-1H-purine-2,6-dione (FIG. 3). Although caffeine occurs naturally, it is prepared synthetically for commercial drug use. Caffeine is the most widely active substance in the world. Average caffeine consumption by adult humans varies among different cultures and nations from 80 to 400 mg per person per day (Daly 1998). Caffeine elicits a diverse number of pharmacological responses, including increased vigilance, decreased psychomotor reaction time, and increased sleep latency and waking time and may also influence intellectual performance (Nehlig 1992). Moreover, caffeine causes relaxation of smooth muscles, enhances the secretion of gastric acid and the release of catecholamines, and increases metabolic activity (Fredholm 1999).

Caffeine is essentially non-toxic. The FDA has indicated that no fatal caffeine poisoning has ever been reported as the result of an overdose of this compound. The short term lethal dose of caffeine in adults is 5-10 grams. At moderate doses, caffeine poses little or no risk of developmental toxicity for the human fetus. These is no evidence that consumption of caffeine is causally related to the development of cancer or increased incidence of coronary heart disease. Caffeine is readily absorbed after oral, rectal or parenteral administration. Maximal plasma concentrations are achieved within 1 hour. Caffeine has a half-life in plasma of 3-7 hours.

Caffeine is the only over-the-counter stimulant that meets the FDA standards for stimulants. The FDA has concurred that caffeine is both safe and effective. The recommended dose is 100-200 mg not to be administered more often than every 3 or 4 hours. The FDA has noted that, in contrast to the irritating qualities of many coffee extracts, caffeine itself, does not cause irritation of the gastrointestinal tract in the usual doses. This is an advantage when the drug is used for its stimulant properties. The FDA, in its publications has stated that the evidence establishes that caffeine restores alertness when a person is drowsy or fatigued.

Although the inhibition of phosphodiesterases may contribute to the actions of caffeine (Daly 1998), there is growing evidence that most pharmacological effects of this xanthine result from antagonism of adenosine receptors designated as $A_1$, $A_{2A}$, $A_{2B}$, and $A_3$ subtypes (Fredholm 1999). Caffeine acts most potently at $A_{2A}$ receptors, followed closely by $A_1$ receptors, then $A_{2B}$ receptors (Klotz 1998; Ongini 1996), and as a weak antagonist at human $A_3$ receptors. Blockade by caffeine of adenosine receptors, namely the $A_1$ and the $A_{2A}$ receptor types, inhibits the action of endogenous adenosine on a variety of physiological processes (Fredholm 1995). Under normal conditions, blood levels of adenosine appear to be sufficient to tonically activate $A_{2A}$ receptors in platelets. Recently, in $A_{2A}$ receptor-knockout mice, it was reported that platelet aggregation was increased, indicating the importance of this receptor subtype in platelet function (Ledent 1997). It is therefore conceivable that caffeine could block these tonically activated $A_{2A}$ receptors in platelets and alter their functions modulated by adenosine.

For many years, an association has been suspected between coffee drinking and cardiovascular diseases, in particular coronary heart disease, but recently it has been demonstrated that coffee or caffeine consumption does not increase the risk of coronary heart diseases or stroke (Grobbee 1990; Jee 1999).

Caffeine is present in several analgesic preparations. To the extent that this is at all rational it may be related to the presence of adenosine $A_{2A}$ receptors in or close to sensory nerve endings that cause hyperalgesia (Ledent et al., 1997). Indeed, caffeine does have hypoalgesic effects in certain types of C-fiber-mediated pain (Myers et al., 1997). The analgesic effects are small (Bättig and Welzl, 1993). Under conditions of pain, however, caffeine could have an indirect beneficial effect by elevating mood and clear-headedness (Lieberman et al., 1987). In this study it was found that both mood and vigilance were more improved by aspirin in combination with caffeine than by aspirin given alone or by placebo. Compositions containing one or more of the analgesics aspirin, acetaminophen and phenacetin in combination with varying amounts of caffeine have been marketed in the past. In several cases, such non-narcotic analgesic/caffeine combination products have further included one of the narcotic analgesics codeine, propoxyphene or oxycodone. Examples of these combinations include the products known commercially as Excedrin™, SK-65™, Darvon™, Anacin™ and with Codeine, Tabloid™ Brand.

It cannot be excluded that caffeine might have analgesic properties for specific types of pain, which may be the case for headache (Ward et al., 1991), which is significantly and dose-dependently reduced by caffeine under double-blind conditions. The effect was similar to that of acetaminophen, which is frequently combined with caffeine, and showed no relation to the effects on mood or to self-reported coffee drinking. As reviewed (Migliardi et al., 1994), patients rate caffeine-containing analgesics as superior to caffeine-free preparations for the treatment of headache. In addition, caffeine may exert an antinociceptive effect in the brain, because it can antagonize pain-related behavior in the mouse following i.c.v. injection (Ghelardini et al., 1997). Moreover, this effect may be related to antagonism of a tonic inhibitory activity of adenosine $A_1$ receptors that reduce cholinergic transmission (cf. Rainnie et al., 1994; Carter et al., 1995).

As noted above, sleep seems to be one of the physiological functions most sensitive to the effects of caffeine in humans. It is well known that caffeine taken at bedtime affects sleep negatively (see Snel, 1993). Generally, more than 200 mg of caffeine is needed to affect sleep significantly. The most prominent effects are shortened total sleep time, prolonged sleep latency, increases of the initial light sleep EEG stages, and decreases of the later deep sleep EEG stages, as well as increases of the number of shifts between sleep stages.

At present, the treatment of choice for premature ejaculation is psychotherapy, either as a behavioural dual team sex therapy according to Master & Johnson protocol, or individual psychotherapy (Rifelli and Moro. Sessuologia Clinica. Bologna, 1989). Previous methods of treating premature ejaculation include psychological therapies, topical anesthetics and the use of devices (U.S. Pat. Nos. 5,535,758, 5,063, 915, 5,327,910, and 5,468,212). All of these methods may have significant drawbacks. Psychological therapies benefit only a subset of patients and require specialized therapists who may not be available to all patients, particularly in remote areas. Furthermore, psychological therapies cannot alleviate premature ejaculation resulting from non-psychological causes. Anesthetic agents decrease sensitivity of tissues, thereby diminishing sexual pleasure. Also, topical anesthetics can be transferred to sexual partners and thereby decrease their sensitivity and pleasure as well. With regard to devices, these can be awkward, inconvenient and embarrassing to use. Devices are highly conspicuous, and reveal the very condition which the suffering partner may prefer to conceal. Additionally, devices can cause irritation to one or both partners.

Methods for treating premature ejaculation by systemic administration of several different antidepressant compounds have been described (U.S. Pat. Nos. 4,507,323, 4,940,731, 5,151,448, and 5,276,042; PCT Publication No. WO95/13072). However, these drugs may not be effective for all patients, and the side effects of these drugs can halt treatment or impair patient compliance. Disease states or adverse interactions with other drugs may contraindicate the use of these compounds or require lower dosages that may not be effective to delay the onset of ejaculation. Additionally, the stigma of mental illness associated with antidepressant therapy can discourage patients from beginning or continuing such treatments. Administration of the antidepressant fluoxetine has been claimed to treat premature ejaculation (U.S. Pat. No. 5,151,448). However, the administration of fluoxetine may have many undesired aspects. Patients with hepatic or renal impairments may not be able to use fluoxetine due to its metabolism in the liver and excretion via the kidney. Systemic events during fluoxetine treatment involving the lungs, kidneys or liver have occurred, and death has occurred from overdoses. In addition, side effects of oral fluoxetine administration include hair loss, nausea, vomiting, dyspepsia, diarrhea, anorexia, anxiety, nervousness, insomnia, drowsiness, fatigue, headache, tremor, dizziness, convulsions, sweating, pruritis, and skin rashes. Fluoxetine interacts with a range of drugs, often by impairing their metabolism by the liver.

U.S. Pat. No. 4,940,731 describes the oral or parenteral administration of sertraline for treating premature ejaculation. It has been recognized that sertraline shares many of the same problems as fluoxetine; (see Martindale, The Extra Pharmacopoeia, 31st edition, at p. 333 (London: The Royal Pharmaceutical Society, 1996)). Sertraline is metabolized in the liver, and is excreted in the urine and feces. Thus, patients with cirrhosis must take lower doses, and caution must be exercised when administering sertraline to patients with renal impairment. Individuals taking monoamine oxidase inhibitors cannot take sertraline due to the risk of toxicity, leading to memory changes, confusion, irritability, chills, pyrexia and muscle rigidity. Side effects resulting from oral sertraline administration include nausea, diarrhea, dyspepsia, insomnia, somnolence, sweating, dry mouth, tremor and mania. Rare instances of coma, convulsions, fecal incontinence and gynecomastia have occurred in patients undergoing sertraline therapy. U.S. Pat. No. 5,276,042 describes the administration of paroxetine for the treatment of premature ejaculation. Paroxetine is predominantly excreted in the urine, and decreased doses are recommended in patients with hepatic and renal impairments. Like sertraline, paroxetine cannot be given to patients undergoing treatment with a monoamine oxidase inhibitor. Side effects from oral administration of paroxetine include hyponatremia, asthenia, sweating, nausea, decreased appetite, oropharynx disorder, somnolence, dizziness, insomnia, tremor, anxiety, impaired micturition, weakness and paresthesia. Thus there is a need for a method of treating premature ejaculation that requires no specialized psychological therapy, can be used conveniently and without embarrassment, and does not involve the problems associated with prior therapeutic methods.

U.S. Pat. No. 6,037,360 discloses that administration of various serotonin agonists and antagonists is effective in the treatment of premature ejaculation. The adverse effects occurring most frequently during treatment with serotonin inhibitors are gastrointestinal disturbances, such as, for example nausea, diarrhoea/loose stools, constipation. (Drugs 43 (Suppl. 2), 1992). Nausea is the main adverse effect in terms of incidence. Moreover it has been frequently observed that after administration of serotonin inhibitors, patients suffer from dyspepsia.

U.S. Pat. No. 5,707,999 teaches that two specific α1-blockers, alfizosine and terazosine, are effective in the treatment of psychogenic premature ejaculation and said drugs turned out to be effective in patients who proved to have no benefit from psychological therapy. However terazosine and its analogs have several side effects including headache, nausea, weight gain, dizziness, somnolence, dyspnea and blurred vision.

U.S. Pat. No. 6,037,346 discloses the local administration of phosphodiesterase inhibitors for the treatment of erectile dysfunction and a preferred mode of administration is claimed as transurethral. Pharmaceutical formulations and kits are provided as well. US application US 2002/0037828 A1 discloses the use of phosphodiesterase inhibitors for treating premature ejaculation.

U.S. Pat. Nos. 4,656,177 and 4,777,174 disclose combinations of non-narcotic analgesics/nonsteroidal anti-inflammatory drugs and/or narcotic analgesics and caffeine. The compositions elicit a more potent and more rapid analgesic response than if the pain reliever is given alone.

U.S. Pat. No. 4,777,174 discloses combinations of non-narcotic analgesics/nonsteroidal anti-inflammatory drugs and/or narcotic analgesics and caffeine. The compositions elicit a more potent and more rapid analgesic response than if the pain reliever is given alone.

U.S. Pat. No. 5,248,678 teaches a method of increasing the arousal and alertness of comatose patients or nea-comatose patients comprising administering to the patients effective amounts of an adenosine receptor antagonist, such as caffeine, and a GABA agonist, such as gabapentin.

Heretofore, there has been no recognition or appreciation that a combination of a μ-opiate analgesic such as tramadol and an analgesia-enhancing amount of dextromethorphan or for that matter, any other NMDA receptor antagonist can be used effectively to treat premature ejaculation in humans. Further, heretofore, there has been no recognition or appreciation that a combination of a μ-opiate analgesic such as tramadol, a cyclic-GMP-specific phosphodiesterase type 5 (PDE5) inhibitor and an analgesia-enhancing amount of dextromethorphan or for that matter, any other NMDA receptor antagonist can be used effectively to treat premature ejaculation in humans. Further, heretofore, there has been no recognition or appreciation that a combination of a μ-opiate analgesic such as tramadol, a cyclic-GMP-specific phosphodiesterase type 5 (PDE5) inhibitor, caffeine and an analgesia-enhancing amount of dextromethorphan or for that matter, any other NMDA receptor antagonist can be used effectively to treat premature ejaculation in humans.

Accordingly, an object of the invention is to provide methods and compositions for the treatment of premature ejaculation which provide without the harmful side effects associated with the currently available therapy. Surprisingly, it has now been found that a combination of a non-toxic NMDA receptor antagonist such as dextromethorphan with a μ-opiate analgesic such as tramadol exhibit significant palliative effects on premature ejaculation. Surprisingly, it has also now been found that a combination of a non-toxic NMDA receptor antagonist such as dextromethorphan with a μ-opiate analgesic such as tramadol and a cyclic-GMP-specific phosphodiesterase type 5 (PDE5) inhibitor such as sildenafil exhibit significant palliative effects on premature ejaculation. These and other objects and features of the invention will be apparent from the following description.

SUMMARY OF THE INVENTION

In one aspect, the present invention provides a method of effectively treating a sexual dysfunction in humans or other mammals. The method comprises administering to a patient in need of such treatment an amount of agents including a) an NMDA receptor antagonist or a pharmaceutically acceptable salt thereof, and b) a μ-opiate analgesic, which is a μ-opiate receptor agonist, partial agonist or agonist/antagonist, or a pharmaceutically acceptable salt thereof. The combined amount of agents is effective to treat the sexual dysfunction.

In accordance with the present invention, the sexual dysfunction can be premature ejaculation or a sexual dysfunction that includes premature ejaculation as a component of the condition.

The agents can be administered separately or in combination. When three or more agents are involved, the agents can be administered in various combinations. For example, three agents can be administered together, or two of the agents can be administered together, while the third agent is administered separately.

The agents are preferably administered prior to sexual activity. Administration can be orally, by means of an implant, parenterally, sub-dermally, sublingually, rectally, topically, or via inhalation. In preferred embodiments, the agents are administered orally.

The NMDA receptor antagonist can be dextromethorphan, dextrorphan, ketamine, amantadine, memantine, eliprodil, ifenprodil, phencyclidine, MK-801, dizocilpine, CCPene, flupirtine, or derivatives or salts thereof. Preferably, the antagonist is dextromethorphan.

The μ-opiate receptor agonist, partial agonist or agonist/antagonist can be any one of (1R,2R or 1S,2S)-(dimethylaminomethyl)-1-(3-methoxyphenyl)-cyclohexanol (tramadol), its N-oxide derivative ("tramadol N-oxide"), and its O-desmethyl derivative ("O-desmethyl tramadol") or mixtures, stereoisomers or recemates thereof. In preferred embodiments, the μ-opiate receptor agonist, partial agonist or agonist/antagonist is tramadol.

The agents can be administered in a dosage form as a tablet, a multiparticulate formulation for oral administration; a solution, a sustained release formulation, a suspension or elixir for oral administration, an injectable formulation, an implantable device, a topical preparation, a solid state and/or depot type transdermal delivery device(s), a suppository, a buccal tablet, or an inhalation formulation such as a controlled release particle formulation or spray, mist or other topical vehicle, intended to be inhaled or instilled into the sinuses. The dosage form can be further defined as a solid oral dosage form formulated as a tablet or capsule.

In accordance with the present invention, the ratio of NMDA receptor antagonist to μ-opiate receptor agonist, partial agonist or agonist/antagonist can be from about 15:1 to 1:15, about 10:1 to 1:10, about 5:1 to 1:5, or about 1:2.

In certain embodiments of the present invention, a phosphodiesterase (PDE) inhibitor or a pharmaceutically acceptable salt thereof is included as one of the agents. Preferably, the PDE inhibitor is a phosphodiesterase type 5 inhibitor. The PDE inhibitor can be sildenafil, aminophylline, theophylline, amrinone, milrinone, vesnarinone, vinpocetine, pemobendan, cilostamide, enoximone, peroximone, rolipram, R020-1724, zaniprast, dipyridamole, MY5445, or IC-351, or pharmaceutically acceptable salts thereof. The ratio of NMDA receptor antagonist to phosphodiesterase inhibitor to μ-opiate receptor agonist, partial agonist or agonist/antagonist can be from about 90:1:1 to 1:90:1 to 1:1:90.

In certain embodiments, a cytochrome P450 inhibitor or a pharmaceutically acceptable salt thereof is included as one of the agents. Preferably, the cytochrome P450 inhibitor is a debrisoquin hydroxylase inhibitor. The inhibitor can be quinidine, quinine, naphthyridine, xanthine, phenoxy amino alkane, carbamoyl imidazole, a guanidine imidazole, cimetidine (N-cyano-N'-methyl-N"-[2[[(5-methyl-1H-imidazol-4 yl)methyl]thio]ethyl]guanidine), a quinoline, chloroquine (7-chloro-4-(4-diethylamino-1-methylbutylamino)quinoline), primaquine (8-(4-amino-1-methylbutylamino)-6-methoxyquinoline), a trifluoromethyl oxime ether, fluvoxamine, also known as 5-methoxy-1-[4-(trifluoromethyl)-phenyl]-1 pentanone 0-(2-aminoethyl) oxime, or pharmaceutically acceptable salts thereof. The ratio of NMDA receptor antagonist to cytochrome P450 inhibitor to μ-opiate receptor agonist, partial agonist or agonist/antagonist can be from about 90:1:1 to 1:90:1 to 1:1:90.

In certain embodiments, caffeine is included as one of the agents.

In further embodiments of the present invention, both a phosphodiesterase inhibitor and a cytochrome P450 inhibitor are included as agents. In further embodiments of the present invention, both a phosphodiesterase inhibitor and caffeine are included as agents. In further embodiments of the present invention, both caffeine and a cytochrome P450 inhibitor are included as agents. In further embodiments of the present invention, both a phosphodiesterase inhibitor, caffeine and a cytochrome P450 inhibitor are included as agents.

In another aspect, the present invention provides a pharmaceutical composition comprising a therapeutically effective amount of a combination of agents. The combination comprises a) an NMDA receptor antagonist or a pharmaceutically acceptable salt thereof, b) a μ-opiate receptor agonist, partial agonist or agonist/antagonist, or a pharmaceutically acceptable salt thereof, and c) a phosphodiesterase type V inhibitor or a pharmaceutically acceptable salt thereof. In certain embodiments, the pharmaceutical composition further comprises caffeine as an agent.

The present invention also provides a pharmaceutical composition comprising a therapeutically effective amount of a combination of agents, the combination comprising a) an NMDA receptor antagonist or a pharmaceutically acceptable salt thereof, b) a μ-opiate receptor agonist, partial agonist or agonist/antagonist, or a pharmaceutically acceptable salt thereof, and c) a cytochrome P450 inhibitor or a pharmaceutically acceptable salt thereof. In certain embodiments, the pharmaceutical composition further comprises caffeine as an agent.

The present invention further provides a pharmaceutical composition comprising a therapeutically effective amount of a combination of agents, the combination comprising a) an NMDA receptor antagonist or a pharmaceutically acceptable salt thereof, b) a μ-opiate receptor agonist, partial agonist or agonist/antagonist, or a pharmaceutically acceptable salt thereof, c) a phosphodiesterase type V inhibitor or a pharmaceutically acceptable salt thereof, and d) a cytochrome P450 inhibitor or a pharmaceutically acceptable salt thereof. In certain embodiments, the pharmaceutical composition further comprises caffeine as an agent.

In another aspect, the present invention provides a pharmaceutical composition comprising a therapeutically effective amount of a combination of agents. The combination comprises a) an NMDA receptor antagonist or a pharmaceutically acceptable salt thereof, b) a μ-opiate receptor agonist, partial agonist or agonist/antagonist, or a pharmaceutically acceptable salt thereof, and c) caffeine.

In accordance with the present invention, Applicants have now developed compositions, (combinations and formulations) which are administered to a human in the treatment of premature ejaculation. These compositions, (combinations and formulations) employ, combine, or incorporate (as the case may be) a plurality of effective non-toxic dosage amounts, each dosage amount comprising an effective non-toxic dosage amount of a drug, for example, a μ-opiate analgesic, for example, tramadol (or salt thereof), an effective non-toxic dosage amount of an NMDA receptor antagonist such as dextromethorphan (preferably dextromethorphan hydrate or salt thereof), a PDE5 inhibitor (e.g., sildenafil) and optionally, an effective non-toxic dosage amount of a cytochrome-P450 inhibitor, for example, quinidine (preferably quinidine hydrate or salt thereof).

Applicants have also developed compositions, (combinations and formulations) which are administered to a human in the treatment of premature ejaculation and erection. These compositions, (combinations and formulations) employ, combine, or incorporate (as the case may be) a plurality of effective non-toxic dosage amounts, each dosage amount comprising an effective non-toxic dosage amount of a drug which inhibits cyclic-GMP-specific phosphodiesterase type 5 (PDE5), for example, sildenafil (or salt thereof), an effective non-toxic dosage amount of an NMDA receptor antagonist such as dextromethorphan (preferably dextromethorphan hydrate or salt thereof), caffeine and an effective non-toxic dosage amount of a μ-opiate analgesic, for example, tramadol (or salt thereof).

Accordingly, a further aspect of the subject invention is the disclosure that a combination of a μ-opiate analgesic such as tramadol, an NMDA receptor antagonist such as dextromethorphan which involves in anti-excitotoxic activity in humans, and optionally a cytochrome P450 inhibitor such as quinidine, is very effective in delaying the onset of ejaculation in male humans.

According to yet another aspect of the invention, applicants have provided pharmaceutical compositions (combinations and formulations) comprising a plurality of dosage amounts each comprising, together with pharmaceutical excipients suitable for oral or parenteral administration, a therapeutically effective amount of agents. The amount is effective to treat and to assist to resolve diseases and conditions of premature ejaculation in the human male in a manner that is non-toxic to the patient. The therapeutically effective dosage amount of agents includes a μ-opiate analgesic, for example tramadol, and an effective non-toxic dosage amount of an NMDA receptor antagonist such as dextromethorphan and/or salts thereof (for example the hydrobromide salt) and/or homologues, analogues, derivatives, complexes, prodrugs, esters, and/or fragments thereof, and optionally an effective non-toxic dosage amount of a cytochrome-P450 inhibitor, for example, quinidine (preferably quinidine hydrate or salt thereof).

It is another aspect of the invention to provide a method wherein each pharmacologically active agent is administered orally. It is a further aspect of the invention to provide a method wherein each pharmacologically active agent is administered parenterally.

The present invention provides a method for treating premature ejaculation, the method comprising administering to an individual in need of such treatment a pharmaceutical formulation containing a μ-opiate analgesic such as tramadol, an NMDA receptor antagonist such as dextromethorphan, and optionally an agent which inhibits the oxidative activity of cytochrome-P450, such as a naphthyridine, xanthine, phenoxy amino alkane, carbamoyl imidazole, guanidine imidazole, e.g. cimetidine (N-cyano-N'-methyl-N''-[2[[(5-methyl-1H-imidazol-4 yl)methyl]thio]ethyl]guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime. Administration of the pharmaceutical formulation is carried out within the context of a predetermined dosing regimen such that the agent is effective in the treatment of premature ejaculation. Drug delivery may be accomplished through any route effective to provide relief from premature ejaculation, including oral, parenteral, buccal, rectal, topical, transdermal, transurethral, and intracavernosal injection.

In accordance with the invention, a pharmaceutical formulation is provided for carrying out the method of the invention. The pharmaceutical formulation comprises an effective amount of a selected μ-opiate analgesic such as tramadol, an NMDA receptor antagonist such as dextromethorphan, optionally, a cytochrome-P450 inhibitor, a pharmacologically acceptable carrier or vehicle, and, optionally (i.e., in topical, transdermal or transurethral formulations), an enhancer. Other types of components may be incorporated into the formulation as well, e.g., excipients, surfactants, preservatives (e.g., antioxidants), stabilizers, enzyme inhibitors, chelating agents, and the like, as will be appreciated by those skilled in the art of pharmaceutical formulation preparation and drug delivery.

Yet another aspect of the subject invention is the disclosure that a combination of cyclic-GMP-specific phosphodiesterase type 5 (PDE5) inhibitors such as sildenafil which facilitates the erection of the penis in humans under sexual stimulation, an NMDA receptor antagonist such as dextromethorphan which involves in anti-excitotoxic activity in humans, a μ-opiate analgesic such as tramadol, and optionally a cytochrome P450 inhibitor such as quinidine, is very effective in delaying the onset of ejaculation in male humans who have erection as well as ejaculation problems.

Thus, according to yet another aspect of the invention, applicants have provided pharmaceutical compositions (combinations and formulations) comprising a plurality of dosage amounts each comprising, together with pharmaceutical excipients suitable for oral or parenteral administration, a therapeutically effective (to treat and to assist to resolve diseases and conditions of premature ejaculation in human male non-toxic to the patient) dosage amount of a drug for example which inhibits cyclic-GMP-specific phosphodiesterase type 5 (PDE5), for example, sildenafil, and an effective non-toxic dosage amount dosage amount of an NMDA receptor antagonist such as dextromethorphan and/or salts thereof (for example the hydrobromide salt) and/or homologues, analogues, derivatives, complexes, prodrugs, esters, and/or fragments thereof, and an effective non-toxic dosage amount of a μ-opiate analgesic such as tramadol and/or salts thereof (for example the hydrobromide salt) and/or homologues, analogues, derivatives, complexes, prodrugs, esters, and/or fragments thereof. Drug delivery may be accomplished through any route effective to provide relief from premature ejaculation, including oral, parenteral, buccal, rectal, topical, transdermal, transurethral, and intracavernosal injection.

As with compositions containing a cytochrome P450 inhibitor, compositions containing a PDE5 inhibitor can also comprise a pharmacologically acceptable carrier or vehicle, and, optionally (i.e., in topical, transdermal or transurethral formulations), an enhancer. Other types of components may be incorporated into the formulation as well, e.g., excipients, surfactants, preservatives (e.g., antioxidants), stabilizers, enzyme inhibitors, chelating agents, and the like, as will be appreciated by those skilled in the art of pharmaceutical formulation preparation and drug delivery.

In practicing the present invention, the NMDA antagonist and/or at least one pharmaceutically acceptable salt thereof can be administered before, simultaneously with, or after administration of the tramadol or other μ-opiate agonist or agonist/antagonist and/or at least one pharmaceutically acceptable salt thereof, such that the dosing interval of the a NMDA antagonist and/or at least one pharmaceutically acceptable salt thereof overlaps with the dosing interval of the tramadol or other μ-opiate agonist or agonist/antagonist and/or at least one pharmaceutically acceptable salt thereof.

Also, the cyclic-GMP-specific phosphodiesterase type 5 (PDE5) inhibitor, the cytochrome P450 inhibitor, and/or at least one pharmaceutically acceptable salt thereof can be administered before, simultaneously with, or after administration of the tramadol or other μ-opiate agonist or agonist/antagonist and/or at least one pharmaceutically acceptable salt thereof and the NMDA antagonist and/or at least one pharmaceutically acceptable salt thereof, such that the dosing interval of the cyclic-GMP-specific phosphodiesterase type 5 (PDE5) inhibitor, the cytochrome P450 inhibitor, and/or at least one pharmaceutically acceptable salt thereof overlaps with the dosing interval of the tramadol or other μ-opiate agonist or agonist/antagonist and/or at least one pharmaceutically acceptable salt thereof and the dosing interval of the NMDA antagonist and/or at least one pharmaceutically acceptable salt thereof. Caffeine may also be administered prior to, during, or after the administration of a PDE5 inhibitor, a μ-opiate antagonist or a cytochrome P450 inhibitor to treat premature ejaculation. An additional advantage in using caffeine in the compositions and methods of the present invention is that it may be used to offset drowsiness or sedation which may be experienced by users of opiate analgesic.

The present invention may be further understood by reference to the embodiments in the following numbered sentences:

1. A method of effectively treating a sexual dysfunction in humans or other mammals, comprising administering to a patient in need of such treatment an amount of agents including a) an NMDA receptor antagonist or a pharmaceutically acceptable salt thereof, and b) a μ-opiate receptor agonist, partial agonist or agonist/antagonist, or a pharmaceutically acceptable salt thereof, whereby the combined amount of said agents is effective to treat the sexual dysfunction.

2. The method of sentence 1, wherein the sexual dysfunction is premature ejaculation.

3. The method of sentence 1, wherein the agents are administered separately.

4. The method of sentence 1, wherein the agents are administered in combination.

5. The method of sentence 1, wherein the agents are administered prior to sexual activity.

6. The method of sentence 1, wherein the agents are administered orally, by means of an implant, parenterally, subdermally, sublingually, rectally, topically, or via inhalation.

7. The method of sentence 6, wherein the agents are administered orally.

8. The method of sentence 1, wherein the NMDA receptor antagonist is dextromethorphan, dextrorphan, ketamine, amantadine, memantine, eliprodil, ifenprodil, phencyclidine, MK-801, dizocilpine, CCPene, flupirtine, or derivatives or salts thereof.

9. The method of sentence 8, wherein the NMDA receptor antagonist is dextromethorphan.

10. The method of sentence 1, wherein the a μ-opiate receptor agonist, partial agonist or agonist/antagonist is any one of (1R,2R or 1S,2S)-(dimethylaminomethyl)-1-(3-methoxyphenyl)-cyclohexanol (tramadol), its N-oxide derivative ("tramadol N-oxide"), and its O-desmethyl derivative ("O-desmethyl tramadol") or mixtures, stereoisomers or recemates thereof.

11. The method of sentence 10, wherein the μ-opiate receptor agonist, partial agonist or agonist/antagonist is tramadol.

12. The method of sentence 1 wherein the agents are administered in a dosage form selected from the group consisting of a tablet, a multiparticulate formulation for oral administration; a solution, a sustained release formulation, a suspension or elixir for oral administration, an injectable formulation, an implantable device, a topical preparation, a solid state and/or depot type transdermal delivery device(s), a suppository, a buccal tablet, or an inhalation formulation such as a controlled release particle formulation or spray, mist or other topical vehicle, intended to be inhaled or instilled into the sinuses.

13. The method of sentence 12, wherein the dosage form is further defined as a solid oral dosage form formulated as a tablet or capsule.

14. The method of sentence 1, wherein the ratio of NMDA receptor antagonist to μ-opiate receptor agonist, partial agonist or agonist/antagonist is from about 15:1 to 1:15.

15. The method of sentence 14, wherein the ratio of NMDA receptor antagonist to μ-opiate receptor agonist, partial agonist or agonist/antagonist is from about 10:1 to 1:10.

16. The method of sentence 15, wherein the ratio of NMDA receptor antagonist to μ-opiate receptor agonist, partial agonist or agonist/antagonist is from about 5:1 to 1:5.

17. The method of sentence 16, wherein the ratio of NMDA receptor antagonist to μ-opiate receptor agonist, partial agonist or agonist/antagonist is about 1:2.

18. The method of sentence 1, wherein a phosphodiesterase inhibitor, or a pharmaceutically acceptable salt thereof, is included as an agent.

19. The method of sentence 18, wherein the phosphodiesterase inhibitor is a phosphodiesterase type V inhibitor.

20. The method of sentence 18, wherein the phosphodiesterase inhibitor is sildenafil, aminophylline, theophylline, amrinone, milrinone, vesnarinone, vinpocetine, pemobendan, cilostamide, enoximone, peroximone, rolipram, R020-1724, zaniprast, dipyridamole, MY5445, or IC-351, or pharmaceutically acceptable salts thereof.

21. The method of sentence 18, wherein the ratio of NMDA receptor antagonist to phosphodiesterase inhibitor to μ-opiate receptor agonist, partial agonist or agonist/antagonist is from about 90:1:1 to 1:90:1 to 1:1:90.

22. The method of sentence 1 or 18, wherein a cytochrome P450 inhibitor, or a pharmaceutically acceptable salt thereof, is included as an agent.

23. The method of sentence 22, wherein the cytochrome P450 inhibitor is a debrisoquin hydroxylase inhibitor.

24. The method of sentence 22 wherein the cytochrome P450 inhibitor is quinidine, quinine, naphthyridine, xanthine, phenoxy amino alkane, carbamoyl imidazole, a guanidine imidazole, cimetidine (N-cyano-N'-methyl-N"-[2[[(5-methyl-1H-imidazol-4 yl)methyl]thio]ethyl]guanidine), a quinoline, chloroquine (7-chloro-4-(4-diethylamino-1-methylbutylamino)quinoline), primaquine (8-(4-amino-1-methylbutylamino)-6-methoxyquinoline), a trifluoromethyl oxime ether, fluvoxamine, also known as 5-methoxy-1-[4-(trifluoromethyl)-phenyl]-1 pentanone 0-(2-aminoethyl) oxime, or pharmaceutically acceptable salts thereof.

25. The method of sentence 22, wherein the ratio of NMDA receptor antagonist to cytochrome P450 inhibitor to μ-opiate receptor agonist, partial agonist or agonist/antagonist is from about 90:1:1 to 1:90:1 to 1:1:90

26. The method of sentence 1, 18 or 22, wherein caffeine is included as an agent.

27. A pharmaceutical composition comprising a therapeutically effective amount of a combination of agents, the combination comprising a) an NMDA receptor antagonist or a pharmaceutically acceptable salt thereof, b) a μ-opiate receptor agonist, partial agonist or agonist/antagonist, or a pharmaceutically acceptable salt thereof, and c) a phosphodiesterase type V inhibitor, or a pharmaceutically acceptable salt thereof.

28. A pharmaceutical composition comprising a therapeutically effective amount of a combination of agents, the combination comprising a) an NMDA receptor antagonist or a pharmaceutically acceptable salt thereof, b) μ-opiate receptor agonist, partial agonist or agonist/antagonist, or a pharmaceutically acceptable salt thereof, and c) a cytochrome P450 inhibitor, or a pharmaceutically acceptable salt thereof.

29. A pharmaceutical composition comprising a therapeutically effective amount of a combination of agents, the combination comprising a) an NMDA receptor antagonist or a pharmaceutically acceptable salt thereof, b) a μ-opiate receptor agonist, partial agonist or agonist/antagonist, or a pharmaceutically acceptable salt thereof, c) a phosphodiesterase type V inhibitor, or a pharmaceutically acceptable salt thereof, and d) a cytochrome P450 inhibitor, or a pharmaceutically acceptable salt thereof.

30. The pharmaceutical composition of sentence 27, 28, or 29, wherein the pharmaceutical composition further comprises caffeine.

31. A pharmaceutical composition comprising a therapeutically effective amount of a combination of agents, the combination comprising a) an NMDA receptor antagonist or a pharmaceutically acceptable salt thereof, b) a μ-opiate receptor agonist, partial agonist or agonist/antagonist, or a pharmaceutically acceptable salt thereof, and c) caffeine.

Additional objects, advantages and novel features of the invention will be set forth in part in the description which follows, and in part will become apparent to those skilled in the art upon examination of the following, or may be learned by practice of the invention.

DESCRIPTION OF ILLUSTRATIVE EMBODIMENTS

Figure 1:
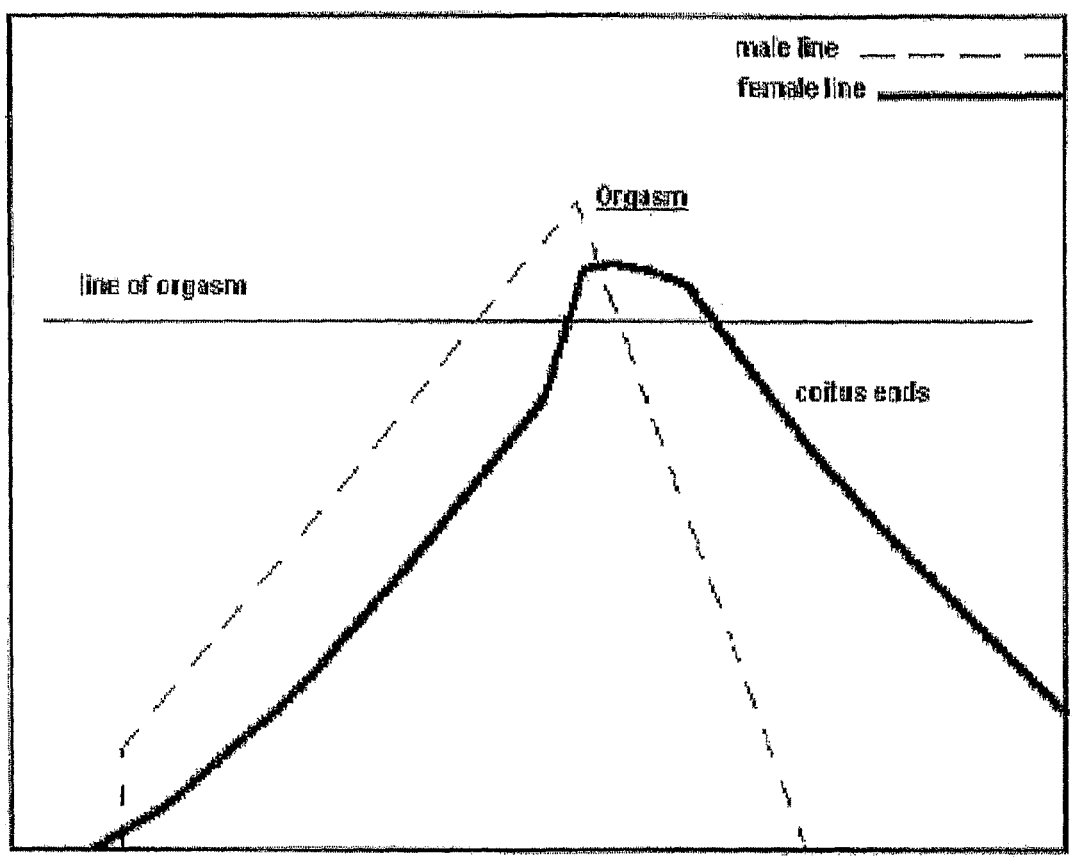
FIG. 1 is a graph showing orgasm levels during normal sexual intercourse. Orgasm levels in a man and woman during normal sexual intercourse are shown. The orgasm level is an arbitrary quantity describing the physical and emotional excitements during sexual intercourse.
Figure 2:
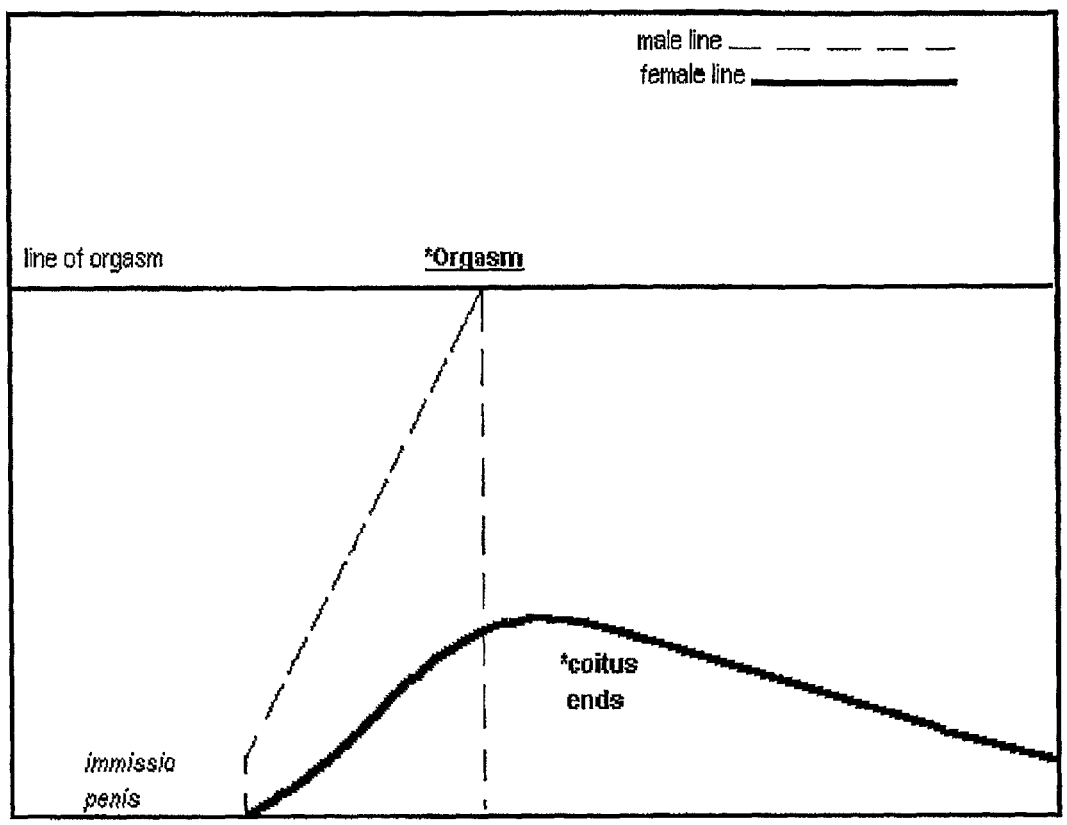
FIG. 2 is a graph showing orgasm levels in the case of premature ejaculation. The orgasm levels in male and female in the case of pre-mature ejaculation are shown. The orgasm level is an arbitrary quantity describing the physical and emotional excitements during sexual intercourse.

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting. It must be noted that, as used in this specification, the singular forms "a," "an" and "the" include plural referents unless the context clearly dictates otherwise. Thus, for example, reference to "a pharmacologically active agent" includes a combination of two or more pharmacologically active agents, and the like. In describing the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect.

The term "topical administration" is used in its conventional sense to mean delivery of a topical drug or pharmacologically active agent to the skin or mucosa.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect.

The term "premature ejaculation" as used herein intends a sexual dysfunction wherein a male is unable to control the ejaculatory process to a degree sufficient to satisfy a partner. Generally, "premature ejaculation" refers to persistent or recurring ejaculation with minimal stimulation before or during sexual intercourse. The term includes both "congenital" or "lifelong" premature ejaculation and "primary" or "acquired" premature ejaculation as set forth, for example, in U.S. Pat. No. 5,151,448, and in Male Infertility and Sexual Dysfunction at p. 356 (New York: Springer-Verlag, 1997). See also Diagnostic and Statistical Manual of Mental Disorders (Washington, D.C.: American Psychiatric Association, 1994).

The term "NSAID" refers to non-steroidal substances which inhibit the production of prostaglandins by binding with cyclo-oxygenase enzymes. The compound acetaminophen is included under this category even though acetaminophen does not have anti-inflammatory properties but bind with cyclo-oxygenase enzymes in the periphery and at the hypothalamic thermoregulatory center.

The term "sildenafil" as used herein includes the free base form of this compound as well as pharmaceutically acceptable acid addition salts thereof formed with organo-carboxylic acids, organo-sulphonic acids or inorganic acids. For purposes of the present invention, the organo-carboxylic acid salt, sildenafil citrate, having a solubility in water of 3.5 mg/ml is particularly preferred. Reference to "sildenafil" includes sildenafil citrate.

The term "caffeine" as used herein is intended to encompass not only caffeine as the anhydrous powder, but any salt or derivative of caffeine or any compounded mixture thereof which is non-toxic, pharmaceutically acceptable and which is capable of hastening and enhancing an analgesic or anti-inflammatory response when employed as described herein (See, for example, The Merck Index, ninth edition, Merck & Co., Inc. Rahway, N.J. (1976), pp. 207-208, for a description of caffeine salts, derivatives and mixtures that may prove useful in the compositions of the present invention). Nevertheless, caffeine as the anhydrous powder base is presently preferred and, where specific amounts of caffeine are set forth below, such amounts are given in mg of the anhydrous base.

The inventors were searching for an effective treatment of premature ejaculation. Based on the previous arts described above the inventors reasoned that in order to control the ejaculation process for males who do not have any erection problem and to have satisfactory sexual intercourse (hereinafter referred to as CLASS I), the ejaculation process has to be delayed so that the sexual partners would have sufficient time for intercourse to reach maximum sexual satisfaction.

In the case of males who have erection problem and can not control ejaculation once erection is achieved the following two steps have to be preferred; (1) the erection has to be achieved through certain pharmaceutical agents such as sildenafil such that the male will have full erection upon the stimulation by the sexual partner; (2) the ejaculation process has to be delayed so that the sexual partners would have sufficient time for intercourse to reach maximum sexual satisfaction (hereinafter referred to as CLASS II).

It is understood that the administration of DM has the anti-excitotoxic effect in humans and the administration of DM to human male would have an effect on the ejaculation process. It is also understood that tramadol has analgesic effect due to their action on the nerve signals. Further it is understood that administration of a debrisoquin hydroxylase inhibitor or a cytochrome-P450 inhibitor concurrently with DM substantially increases the observable therapeutic effects of DM in human clinical trials, then the effectiveness of DM as an agent for treating premature ejaculation can also be increased by the co-administration of a cytochrome oxidase inhibitor. Based on these observations the inventors reasoned that administration of a combination of these agents would have a therapeutical effect on premature ejaculation for CLASS I males. To their surprise, they now discovered that ingestion of these agents indeed has profound effects on the premature ejaculation and that they prolong the sexual intercourse to reach maximal orgasm. Further they observed that these agents can be used to have multiple orgasm during sexual intercourse.

In addition, the inventors have discovered that ingestion of sildenafil, tramadol and DM has profound effects on the premature ejaculation in CLASS II males and that they prolong the sexual intercourse to reach maximal orgasm. Further they observed that these agents can be used to have multiple orgasm during sexual intercourse. Further the inventors have discovered that ingestion of tramadol along with sildenafil and DM does not affect the therapeutical effect of sildenafil and DM combination in treating premature ejaculation in CLASS II patients.

Additionally, in certain embodiments of the present invention, the addition of caffeine to the above composition has the advantage to offset the drowsiness or sedation experienced by some of the users of opiate analgesic.

Active Agents for Treating Premature Ejaculation in CLASS I Males

In order to carry out the method of the invention to treat premature ejaculation in CLASS I males, selected pharmacologically active agent(s) is administered to an individual. The active agents may be administered orally, parenterally, buccally, rectally, or locally by intracavernosal injection or by delivery to the urethra. Suitable pharmacologically active agents include: μ-opiate analgesic tramadol, its metabolites, salts thereof.

(+/−)-Tramadol is a synthetic 4-phenyl-piperidine analogue of codeine (Shipton E A 2000). It is a central analgesic with a low affinity for opiate receptors. Its selectivity for mu receptors has recently been demonstrated, and the M1 metabolite of tramadol, produced by liver O-demethylation, shows a higher affinity for opiate receptors than the parent drug. The rate of production of this M1 derivative (O-demethyl tramadol), is influenced by a polymorphic isoenzyme of the debrisoquine-type, cytochrome P450 2D6 (CYP2D6). One mechanism relates to its weak affinity for μ-opiate receptors (6,000-fold less than morphine, 100-fold less than d-propoxyphene, 10-fold less than codeine, and equivalent to dextromethorphan). Moreover, and in contrast to other opiates, the analgesic action of tramadol is only partially inhibited by the opiate antagonist naloxone, which suggests the existence of another mechanism of action. This was demonstrated by the discovery of a monoaminergic activity that inhibits noradrenaline (norepinephrine) and serotonin (5-hydroxytryptamine; 5-HT) reuptake, making a significant contribution to the analgesic action by blocking nociceptive impulses at the spinal level (Dayer et al. 1994 & 1997).

(+/−)-Tramadol is a racemic mixture of 2 enantiomers, each one displaying differing affinities for various receptors. (+/−)-tramadol is a selective agonist of μ receptors and preferentially inhibits serotonin reuptake, whereas (−)-tramadol mainly inhibits noradrenaline reuptake. The action of these 2 enantiomers is both complementary and synergistic and results in the analgesic effect of (+/−)-tramadol. After oral administration, tramadol demonstrates 68% bioavailability, with peak serum concentrations reached within 2 hours. The elimination kinetics can be described as 2-compartmental, with a half-life of 5.1 hours for tramadol and 9 hours for the M1 derivative after a single oral dose of 100 mg. This explains the approximately 2-fold accumulation of the parent drug and its M1 derivative that is observed during multiple dose treatment with tramadol. The recommended daily dose of tramadol is between 50 and 100 mg every 4 to 6 hours, with a maximum dose of 400 mg/day. The duration of the analgesic effect after a single oral dose of tramadol 100 mg is about 6 hours. Adverse effects, and nausea in particular, are dose dependent and therefore considerably more likely to appear if the loading dose is high. The reduction of this dose during the first days of treatment is an important factor in improving tolerability. Other adverse effects are generally similar to those of opiates, although they are usually less severe, and can include respiratory depression, dysphoria and constipation. Tramadol can be administered concomitantly with other analgesics, particularly those with peripheral action, while drugs that depress CNS function may enhance the sedative effect of tramadol. Tramadol has pharmacodynamic and pharmacokinetic properties that are highly unlikely to lead to dependence. This was confirmed by various controlled studies and postmarketing surveillance studies, which reported an extremely small number of patients developing tolerance or instances of tramadol abuse (Raffa et al. 1993; Lee et al. 1993)

In certain embodiments of the present invention, premature ejaculation may be treated without the harmful side effects associated with traditional analgesics, such as respiratory depression, disturbed sleep patterns, diminished appetite, seizures, and psychological and/or physical dependency.

Although it has proven to be a safe and effective agent for the control of pain, adverse effects can occur with its use. It has been reported the occurrence of seizure activity after the inadvertent administration of 4 mg/kg of tramadol to a child (Tobias 1997).

Dextromethorphan acts at a class of neuronal receptors known as sigma receptors. They are inhibitory receptors, meaning that their activation by DM or other sigma agonists causes the suppression of certain types of nerve signals. Dextromethorphan also acts at another class of receptors known as N-methyl-D-aspartate (NMDA) receptors, which are one type of excitatory amino acid (EAA) receptor. Unlike its agonist activity at sigma receptors, DM acts as an antagonist at NMDA receptors, which means that DM suppresses the transmission of nerve impulses mediated via NMDA receptors. Since NMDA receptors are excitatory receptors, the activity of DM as an NMDA antagonist also leads to the suppression of certain types of nerve signals. The anti-excitotoxic activity of dextromethorphan and dextrorphan, and the blockade of NMDA receptors by these drugs, are discussed in items such as Choi 1987, Wong et al 1988, Steinberg et al 1988, and U.S. Pat. No. 4,806,543 (Choi 1989). Dextromethorphan has also been reported to suppress activity at neuronal calcium channels (Carpenter et al 1988). Dextromethorphan and the receptors it interacts with are further discussed in Tortella et al 1989, Leander 1989, Koyuncuoglu & Saydam 1990, Ferkany et al 1988, George et al 1988, Prince & Feeser 1988, Feeser et al 1988, Craviso and Musacchio 1983, and Musacchio et al 1988.

DM disappears fairly rapidly from the bloodstream (see, e.g., Vetticaden et al 1989 and Ramachander et al 1977). DM is converted in the liver to two metabolites called dextrorphan and 3-methoxymorphinan, by an enzymatic process called O-demethylation. This enzyme is usually referred to as debrisoquin hydroxylase, since it was discovered a number of years ago to carry out a hydroxylation reaction on debrisoquin. It is also referred to in various articles as P450DB or P450-2D6. A number of compounds inhibit the activity of the debrisoquin hydroxylase (sparteine monooxygenase) isozyme; see Inaba et al 1985. The most powerful of these inhibitors is quinidine, a dextrorotatory stereoisomer of quinine; it is normally used to treat cardiac arrhythmias. Inaba et al 1986 and Nielsen et al 1990 discuss the ability of quinidine to inhibit the oxidation of sparteine in in vivo animal tests, and Brinn et al 1986, Brosen et al 1987, and Broly et al 1989 discuss the ability of quinidine to inhibit DM metabolism in liver cell preparations. In addition to the inhibition of debrisoquin hydroxylase, which is exceptionally potent and easily demonstrated, other cytochrome P450 isozymes are also likely to be suppressed by quinidine, with varying levels of binding affinity. Accordingly, even though quinidine exerts its most marked effect on debrisoquin hydroxylase, it is likely to suppress a number of other cytochrome P450 enzymes as well, thereby subjecting a patient to a more general loss of normal and desirable liver activity. The primary oxidized metabolic product of dextromethorphan is dextrorphan, which is widely believed among neurologists to be active in exactly the same manner as dextromethorphan; both drugs reportedly are sigma agonists, NMDA antagonists, and calcium channel antagonists. It has been shown that the administration of a compound which inhibits debrisoquin hydroxylase, in conjunction with DM, causes a major increase in the concentration and stability of DM in the blood of patients, compared to patients who receive only DM; and the administration of a debrisoquin hydroxylase inhibitor in conjunction with DM has a clear and substantial impact on the detectable effects of DM in humans. Even though debrisoquin hydroxylase inhibitors are preferred in the potentiating activity of Dextromethorphan, other agents which inhibit the oxidative activity of cytochrome-P450, such as a naphthyridine, xanthine, phenoxy amino alkane, carbamoyl imidazole, guanidine imidazole, e.g. cimetidine (N-cyano-N'-methyl-N"-[2[[(5-methyl-1H-imidazol-4 yl)methyl]thio]ethyl] guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime may be useful in potentiating the activity of dextromethorphan.

Caffeine is present in several analgesic preparations. To the extent that this is at all rational it may be related to the presence of adenosine $A_{2A}$ receptors in or close to sensory nerve endings that cause hyperalgesia (Ledent et al., 1997). Indeed, caffeine does have hypoalgesic effects in certain types of C-fiber-mediated pain (Myers et al., 1997). The analgesic effects are small (Bättig and Welzl, 1993). Caffeine could have an indirect beneficial effect by elevating mood and clear-headedness (Lieberman et al., 1987). In this study it was found that both mood and vigilance were more improved by aspirin in combination with caffeine than by aspirin given alone or by placebo.

As reviewed (Migliardi et al., 1994), patients rate caffeine-containing analgesics as superior to caffeine-free preparations for the treatment of headache. In addition, caffeine may exert an antinociceptive effect in the brain, because it can antagonize pain-related behavior in the mouse following i.c.v. injection (Ghelardini et al., 1997). Moreover, this effect may be related to antagonism of a tonic inhibitory activity of adenosine $A_1$ receptors that reduce cholinergic transmission (Rainnie et al., 1994; Carter et al., 1995).

As noted above, sleep seems to be one of the physiological functions most sensitive to the effects of caffeine in humans. It is well known that caffeine taken at bedtime affects sleep negatively (see Snel, 1993). Generally, more than 200 mg of caffeine is needed to affect sleep significantly. The most prominent effects are shortened total sleep time, prolonged sleep latency, increases of the initial light sleep EEG stages, and decreases of the later deep sleep EEG stages, as well as increases of the number of shifts between sleep stages.

In order to practice the invention, a non-limiting list of μ-opiate analgesic drugs which may be utilized in the present invention include tramadol, metabolites thereof, salts thereof, complexes thereof.

NMDA antagonists which may be utilized in the present invention include dextromethorphan, ketamine and amantidine, as well as metabolites, salts and complexes thereof.

A non-limiting list of caffeine analogs which may be used in the present invention include xanthine, hypoxanthine (6-hydroxypurine), 1-methylxanthine, 3-methylxanthine, 7-methylxanthine, azaxanthine (8-aza-2,6-dihydroxypurine), theophylline and theobromine.

Oral combination dosage units preferably contain dextromethorphan in the range of about 30 to not more than 200 milligrams (mg), preferably in the range of about 60 and about 120 mg and of tramadol in the range of about 30 to about 500 mg, preferably in the range of about 30 to about 200 mg, so long as the combined dose received by the patient is accompanied by minimal or substantially no undesirable side effects. Caffeine may be included in the composition at a dosage of about 30 to not more than 200 mg, preferably in the range of about 60 mg and about 100 mg.

A particularly preferred oral combination dosage unit contains about 120 mg dextromethorphan and not more than 100 mg tramadol, more preferably about 90 mg dextromethorphan and not more than about 100 mg tramadol. Another preferred oral combination dosage unit contains about 120 mg dextromethorphan, about 100 mg of caffeine and not more than 100 mg tramadol, more preferably about 90 mg dextromethorphan, about 60 mg of caffeine and not more than about 100 mg tramadol.

Alternatively, the dextromethorphan and tramadol may be formulated separately in the foregoing compositions as the sole active ingredient for practicing sequential administration of each respective drug.

Alternatively, the dextromethorphan, caffeine and tramadol may be formulated separately in the foregoing compositions as the sole active ingredient for practicing sequential administration of each respective drug.

For sequential administration therapy, tramadol, caffeine and dextromethorphan each is administered in a separate dosage. For sequential administration of tramadol, the dosage unit preferably contains tramadol in a range of about 10 to about 500 mg, more preferably in the range of about 20 mg to about 300 mg, for administration of caffeine, the dosage unit preferably contains caffeine in a range of about 10 to about 400 mg, more preferably in the range of about 30 mg to about 200 mg and for administration of dextromethorphan the dosage unit preferably contains dextromethorphan in a range of about 30 to not more than 120 mg, more preferably in the range of about 60 to about 90 mg so long as the total combined dose received by the patient is accompanied by minimal or substantially no undesirable side effects.

A particularly preferred sequential administration dosage unit contains tramadol in the range of about 30 to about 100 mg and of dextromethorphan contains dextromethorphan in the range of about 30 to about 135 mg. Preferably, each drug is administered orally. Alternatively, each drug can be administered by different oral routes; i.e., one can be ingested and the other administered sublingually or by buccal patch.

For effective sequential administration of tramadol, caffeine and dextromethorphan, the release of each drug is preferably staggered to maximize the beneficial delayed ejaculation by dextromethorphan.

A particularly preferred sequential administration dosage unit contains tramadol in the range of about 30 to about 100 mg, caffeine in the range of 30 to 100 mg and dextromethorphan in the range of about 30 to about 135 mg. Preferably, each drug is administered orally. Alternatively, each drug can be administered by different oral routes; i.e., one can be ingested and the other administered sublingually or by buccal patch.

For effective sequential administration of tramadol, caffeine and dextromethorphan, the release of each drug is preferably staggered to maximize the beneficial delayed ejaculation by dextromethorphan.

In order to potentiate the effect of dextromethorphan, optionally an effective amount of a cytochrome P450 enzyme inhibitor such as quinidine can be administered to the patient either in a combination dosage unit or in a sequential administration dosage unit. When a cytochrome P450 inhibitor is administered in order to augment the effect of dextromethorphan, the dosage of dextromethorphan can be suitably adjusted to have maximum efficacy with minimum side effects. Oral combination dosage units preferably can contain quinidine in the range of about 50 to not more than 200 milligrams (mg), preferably in the range of from about 90 to about 120 mg.

Active Agents for Treating Premature Ejaculation in CLASS II Males

In order to carry out the method of the invention to treat premature ejaculation in CLASS II males who have erection as well as ejaculation problems, selected pharmacologically active agent is administered to an individual. The active agents may be administered orally, parenterally, buccally, rectally, or locally by intracavernosal injection or by delivery to the urethra. Suitable pharmacologically active agents include, cyclic-GMP-specific phosphodiesterase type 5 (PDE5) inhibitors such as sildenafil, caffeine, anti-excitotoxic agents such as dextromethorphan, a µ-opiate analgesic such as tramadol and optionally the cytochrome-P450 inhibitors such as quinine, quinidine, naphthyridine, xanthine, phenoxy amino alkane, carbamoyl imidazole, guanidine imidazole, e.g. cimetidine (N-cyano-N'-methyl-N'''-[2[[(5-methyl-1H-imidazol-4 yl)methyl]thio]ethyl]guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime.

Figure 3:
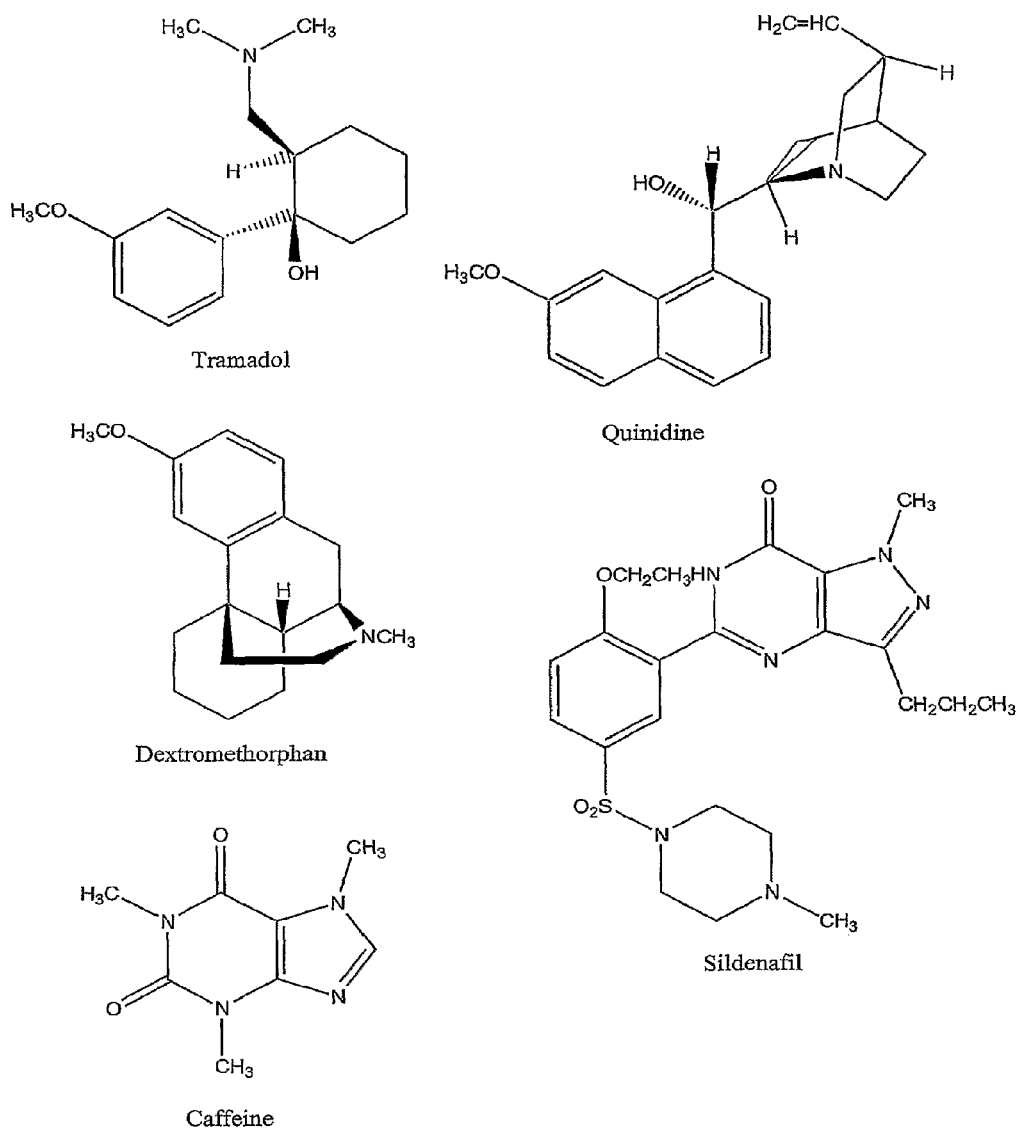
FIG. 3 provides the chemical structures of tramadol, quinidine, dextromethorphan, caffeine, and sildenafil.

Sildenafil is designated chemically as 1-[[3-(6,7-dihydro-1-methyl-7-oxo-3-propyl-1H-pyrazolo[4,3-d]pyrimidin-5-yl)-4-ethoxyphenyl]sulfonyl]-4-methyl piperazine and has the following structural formula: FIG. 3

Sildenafil citrate is presently the active ingredient of a commercial medication for impotence sold under the designation Viagra™ (Pfizer Labs, N.Y.) formulated in tablets equivalent to 25 mg, 50 mg and 100 mg sildenafil for oral administration. According to the manufacturer, in addition to the active ingredient, sildenafil citrate, each tablet contains the following inactive ingredients: microcrystalline cellulose, anhydrous dibasic calcium phosphate, croscarmellose sodium, magnesium stearate, hydroxypropyl methylcellulose, titanium dioxide, lactose, triacetin, and FD&C Blue #2 aluminum lake.

It is known from in vitro studies that sildenafil is approximately 4,000 fold more selective for inhibiting phosphodiesterase type 5 (PDE5) than on other known phosphodiesterases, such as PDE3, which is involved in control of cardiac contractility. Sildenafil is reportedly only about 10-fold as potent for PDE5 compared to PDE6, an enzyme found in the retina and it is this lower selectivity which is thought to be the basis for abnormalities related to color vision observed with higher doses or plasma levels.

Sildenafil, administered as the commercially available Viagra™ formulation, is reported to be rapidly absorbed after oral administration, with absolute bioavailability of about 40%. Its pharmacokinetics are dose-proportional over the recommended dose range. Based on the Viagra™ manufacturer's product literature, maximum observed plasma concentrations are reached within 30 to 120 minutes (median 60 minutes) of oral dosing in the fasted state. When the Viagra™ formulation is taken with a high fat meal, the rate of absorption is reduced, with a mean delay in Tmax of 60 minutes and mean reduction in Cmax of 29%. The mean steady state volume of distribution (Vss) for sildenafil is reportedly 105 L, indicating distribution into the tissues. Based upon reported measurements of sildenafil in the semen of healthy volunteers 90 minutes after dosing, less than 0.001% of the administered dose appeared in the semen of the patients.

Surprisingly, a therapeutically effective dosage combination of dextromethorphan, tramadol and sildenafil employed with the compositions of this invention maximizes the beneficial erectogenic efficacy of sildenafil by delaying the premature ejaculation.

Oral combination dosage units preferably contain dextromethorphan in the range of about 10 to not more than 300 milligrams (mg), preferably in the range of about 30 and about 200 mg, tramadol in the range of about 10 to not more than 200 milligrams (mg), preferably in the range of about 30 and about 150 mg and of sildenafil in the range of about 10 to about 150 mg, preferably in the range of about 15 to about 100 mg, so long as the combined dose received by the patient is accompanied by minimal or substantially no undesirable side effects. A particularly preferred oral combination dosage unit contains about 150 mg dextromethorphan, not more than 200 mg of tramadol, more preferably about 100 mg of tramadol and not more than 150 mg sildenafil, more preferably about 135 mg dextromethorphan, about 100 mg of tramadol and not more than about 100 mg sildenafil.

Alternatively, the dextromethorphan, tramadol and sildenafil may be formulated separately in the foregoing compositions as the sole active ingredient for practicing sequential administration of each respective drug.

For sequential administration therapy, sildenafil, tramadol and dextromethorphan each is administered in a separate dosage. For sequential administration of sildenafil, the dosage unit preferably contains sildenafil in a range of about 10 to about 300 mg, more preferably in the range of about 25 to about 200 mg, for administration of tramadol, the dosage unit preferably contains tramadol in a range of about 20 to not more than 400 mg, more preferably in the range of about 30 to about 200 mg and for administration of dextromethorphan the dosage unit preferably contains dextromethorphan in a range of about 30 to not more than 500 mg, more preferably in the range of about 60 to about 300 mg so long as the total combined dose received by the patient is accompanied by minimal or substantially no undesirable side effects.

A particularly preferred sequential administration dosage unit of sildenafil contains sildenafil in the range of about 50 to about 150 mg, of tramadol contains tramadol in the range of about 50 to about 200 mg and of dextromethorphan contains dextromethorphan in the range of about 45 to about 200 mg. Preferably, each drug is administered orally. Alternatively, each drug can be administered by different oral routes; i.e., one can be ingested and the other administered sublingually or by buccal patch.

If desired, to facilitate absorption and thus bioavailability, absorption enhancing agents, such as cyclodextrins, particularly β-cyclodextrin, or a derivative thereof, such as hydroxypropyl-β-cyclodextrin (HPBCD) and the like may be included. Cyclodextrins are a group of cyclic, nonreducing oligosaccharides built up from six, seven or eight glucopyranose rings, respectively known as alpha, beta and gamma cyclodextrins. The cyclodextrins are a class of cavity-containing cyclic compounds possessing the property of forming a molecular inclusion complexes, which anchor or entrap another chemical compounds without the formation of covalent bonds. HPBCD is a cyclic polymer having a doughnut-shaped molecular structure including an inner cavity.

Hydroxypropyl-β-cyclodextrins are commercially available compounds that are derived from β-cyclodextrins by condensation with a propylene oxide to provide the corresponding hydroxypropyl derivatives having a degree of substitution (D.S.) of up to about 15 or higher. For the purposes of the present invention a D.S. value of about 5 to 7 is preferred.

The preparation of such suitable hydroxypropyl-β-cyclodextrins is described, inter alia, in the International Journal of Pharmaceutics, 29, 73-82 (1986) and in the Journal of Pharmaceutical Sciences, 75 (6), 571-572 (1986). Also known and suitable for the present invention are the hydroxypropyl-β-cyclodextrins that are polyethers of cyclodextrins and are obtained by the condensation of an excess of hydroxypropylene oxide with β-cyclodextrin as described in U.S. Pat. No. 3,459,731, to Gramera et al. Hydroxypropyl-β-cyclodextrin (HPBCD) is particularly preferred cyclodextrin constituent, but is not limited thereto. The weight percent of the HPBCD in the composition is preferably in the range of about 1 to about 10 weight percent of the total composition.

Particularly in the case of sildenafil, it has been found that HPBCD enhances bioavailability. Thus, the desired therapeutic effect can be achieved with a relatively lower dose of sildenafil, thereby minimizing the likelihood of adverse affects.

For effective sequential administration of sildenafil, tramadol and dextromethorphan, the release of each drug is preferably staggered to maximize the beneficial prolongation of erection by dextromethorphan and tramadol and maintenance of erection by sildenafil upon sexual stimulation.

To augment the beneficial effect of dextromethorphan, tramadol and sildenafil therapy, lesser amounts of erectogenic agents can be included. The term "erectogenic agents" as used herein refers to adrenal steroids, such as testosterone, dehydroepiandrosterone (DHEA) and the like. Preferably, the erectogenic agents are added in an amount in the range of about 5 to about 10 percent by weight, more preferably in the range of about 6 to about 8 percent by weight of the weight of sildenafil administered.

To offset the drowsiness or sedation experienced by some of the users of opiate analgesic, caffeine can be added in the composition.

In order to potentiate the effect of dextromethorphan, optionally an effective amount of a cytochrome P450 enzyme inhibitor such as quinidine can be administered to the patient either in a combination dosage unit or in a sequential administration dosage unit. When a cytochrome P450 inhibitor is administered in order to augment the effect of dextromethorphan, the dosage of dextromethorphan can be suitably adjusted to have maximum efficacy with minimum side effects. Oral combination dosage units preferably can contain quinidine in the range of about 50 to not more than 200 milligrams (mg), preferably in the range of about 90 and about 120 mg. Oral combination dosage units preferably can contain quinidine in the range of about 50 to not more than 200 milligrams (mg), preferably in the range of about 90 and about 120 mg.

The active agents may be administered in the form of pharmaceutically acceptable salts, esters, amides or prodrugs or combinations thereof. However, conversion of inactive ester, amide or prodrug forms to an active form must occur prior to or upon reaching the target tissue or cell. Salts, esters, amides and prodrugs of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base (typically wherein the neutral form of the drug has a neutral—NH2 group) using conventional means, involving reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, ptoluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties which may be present on a drug are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature. In addition, chiral active agents may be in enantiomerically pure form, or they may be administered as an enantiomeric mixture.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drugs in combination with a pharmaceutically acceptable carrier and, in addition, may include other pharmaceutical agents, adjuvants, diluents, buffers, etc. The compounds may thus be administered orally, parenterally, transdermally, rectally, nasally, buccally, topically or via an implanted reservoir in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine sodium acetate, triethanolamine oleate, etc. Actual methods of preparing such dosage forms are known, or will be apparent, to those skilled in this art; for example, see Remington's Pharmaceutical Sciences, referenced above. For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. A more recently revised approach for parenteral administration involves use of a slow release or sustained release system, such that a constant level of dosage is maintained. See, e.g., U.S. Pat. No. 3,710,795.

The active agent can be administered in a pharmaceutical formulation suitable for transurethral drug delivery. The formulation contains one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred. Depending on the drug administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co. Irvine, Calif.), SEPA® (available from Macrochem Co., Lexington, Mass.), alcohols (e.g., ethanol), detergents (such as Tergitol®, Nonoxynol-9® and TWEEN-80®) and the like.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Capsule Formulations

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

|  | In each | In 100 |
|---|---|---|
| Capsule Formulation 1 | | |
| Dextromethorphan | 30 mg | 3.0 g |
| Tramadol Hydrochloride | 15 mg | 1.5 g |
| Starch (potato) | 50 mg | 5.0 g |
| Mannitol USP | 40 mg | 4.0 g |
| Microcrystalline Cellulose$^a$ | 50 mg | 5.0 g |
| Stearic acid | 10 mg | 1.0 g |
| Silica gel | 5 mg | 0.5 g |
| Total Solid | 200 mg | 20.0 g |
| Capsule Formulation 2 | | |
| Dextromethorphan | 45 mg | 4.5 g |
| Tramadol Hydrochloride | 20 mg | 2.0 g |
| Starch (potato) | 60 mg | 6.0 g |
| Mannitol USP | 50 mg | 5.0 g |
| Microcrystalline Cellulose$^a$ | 50 mg | 5.0 g |
| Stearic acid | 10 mg | 1.0 g |
| Silica gel | 5 mg | 0.5 g |
| Total Solid | 250 mg | 25.0 g |
| Capsule Formulation 3 | | |
| Dextromethorphan | 45 mg | 4.5 g |
| Tramadol Hydrochloride | 25 mg | 2.5 g |
| Caffeine USP | 30 mg | 3.0 g |
| Starch (potato) | 50 mg | 5.0 g |
| Sucrose USP | 40 mg | 4.0 g |
| Microcrystalline Cellulose$^a$ | 40 mg | 4.0 g |
| Stearic acid | 5 mg | 0.5 g |
| Silica gel | 5 mg | 0.5 g |
| Total Solid | 250 mg | 25.0 g |

EXAMPLE 2

Capsule Formulations Containing Sildenafil

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

|  | In each | In 100 |
|---|---|---|
| Capsule Formulation 1 | | |
| Sildenafil Citrate | 25 mg | 2.5 g |
| Dextromethorphan | 45 mg | 4.5 g |
| Tramadol Hydrochloride | 20 mg | 2.0 g |
| Starch (potato) | 60 mg | 6.0 g |
| Mannitol USP | 50 mg | 5.0 g |

-continued

|  | In each | In 100 |
| --- | --- | --- |
| Microcrystalline Cellulose*a* | 48 mg | 4.8 g |
| Stearic acid | 10 mg | 1.0 g |
| Silica gel | 2 mg | 0.2 g |
| Total Solid | 250 mg | 25.0 g |

Capsule Formulation 2

|  | In each | In 100 |
| --- | --- | --- |
| Sildenafil Citrate | 25 mg | 2.5 g |
| Dextromethorphan | 30 mg | 3.0 g |
| Tramadol Hydrochloride | 15 mg | 1.5 g |
| Starch (potato) | 60 mg | 6.0 g |
| Mannitol USP | 50 mg | 5.0 g |
| Microcrystalline Cellulose*a* | 58 mg | 5.8 g |
| Stearic acid | 10 mg | 1.0 g |
| Silica gel | 2 mg | 0.2 g |
| Total Solid | 250 mg | 25.0 g |

Capsule Formulation 3

|  | In each | In 100 |
| --- | --- | --- |
| Sildenafil Citrate | 25 mg | 2.5 g |
| Dextromethorphan | 45 mg | 4.5 g |
| Tramadol Hydrochloride | 25 mg | 2.5 g |
| Caffeine | 30 mg | 3.0 g |
| Starch (potato) | 60 mg | 6.0 g |
| Sucrose USP | 65 mg | 6.5 g |
| Microcrystalline Cellulose*a* | 58 mg | 5.8 g |
| Stearic acid | 10 mg | 1.0 g |
| Silica gel | 7 mg | 0.7 g |
| Total Solid | 325 mg | 32.5 g |

EXAMPLE 3

The subject was a 40 year old white male in good health. The subject had expressed satisfaction with his sexual activity but desired additional 'staying power'. The subject took two capsules of the test article, the capsule formulation 1 in example 2, approximately 1 hour before engaging in sexual activity. The subject reported that he was able to delay his climax by merely exerting his will. He related that he was able to continue intercourse for as long as he was physically able to perform the necessary motions.

EXAMPLE 4

The subject was a 31 year old white male in excellent health. The subject took two capsules of the test article, the capsule formulation 2 in example 1, approximately three hours before commencing sexual activity. The subject reported that his stamina was significantly increased and that he had achieved two climaxes without an intervening flaccid period.

EXAMPLE 5

A white male of 49 years old was in the process of establishing a business and manufacturing several products, making strategy for securing capital for the company and marketing the product. He used to work long hours a day. He noticed that during sexual activities with his girl friend he could not control the ejaculation resulting in disappointment from his female partner. Because of the premature ejaculation problem he was trying to avoid sexual contact with his female partner whenever possible and his partner was feeling unfulfilled sexual experience and sometimes anger. The patient was provided with capsules of formulation 1 in example 2 and advised to take 2 capsule approximately 3 hours before intercourse and 1 capsule approximately 1 hour before intercourse. He took 2 capsules in the first night and according to his testimony, he felt slightly numb in his penis and he was able to arouse his female partner's sexual feelings by performing pre-intercourse sexual conducts and his partner was able to perform pre-intercourse sexual conducts with his penis for almost half hour without any ejaculation. He was able to perform intercourse for more than 20 minutes and his partner felt exhaustion. His female partner was so ecstatic and he was able to perform sexual intercourse 2 times that night. The patient is periodically taking the capsules whenever he wants to have a good and sound sexual intercourse for his otherwise stressful body.

EXAMPLE 6

A white male of 40 yrs old who is living with his girl friend was keenly interested in the effect of the compositions of the present invention on his sexual activity. The subject consumed two capsule described as formulation 1 in example 2 at approximately 18:00. At 18:45 the subject reported a feeling of heaviness in the genitals with a slight feeling of flushing in the face. Sexual activity commenced at 19:15. Subject reported that his erection had a greater degree of stiffness and a sense of increased distension over that usually experienced. The subject reported that his staying power was increased by approximately 70% over his usual experience. Sexual intercourse was continued for approximately 90 minutes concluding with a more powerful than usual orgasm.

EXAMPLE 7

The Effect of Sildenafil, Dextromethorphan and Tramadol on CLASS II Males

In order to demonstrate the efficacy of sildenafil, tramadol and dextromethorphan composition to treat premature ejaculation on CLASS II males, 30 volunteers have been chosen from the age groups of 21 and 57 who had premature ejaculation and erection problems. The volunteers were given capsules of formulation 1 in example 2. The volunteers were asked to take 2 capsules 2-3 hours before the sexual act and were asked to fill out the form provided in Table before and after the sexual acts. The study was conducted for 8 weeks and the results were compiled and analyzed for sexual satisfaction. The results show that more than 80% of the volunteers were extremely satisfied with the composition of the invention for pre-mature ejaculation problems.

The following publications are incorporated in pertinent part by reference herein.

REFERENCES

1. Albers, G W et al, "Safety and tolerance of oral dextromethorphan in patients at risk for brain ischemia," Stroke 22: 1075-1077 (1991).
2. Applebaum, J S et al, "Dextromethorphan in the treatment of ALS: A pilot study," Abstract number 960S (page 393) in Neurology 41 (Suppl, 1), March 1991
3. Balon, "Antidepressants in the Treatment of Premature Ejaculation," Journal of Sex & Marital Therapy, 22(2):85-96 (1996).
4. Brinn R et al, "Sparteine oxidation is practically abolished in quinidine-treated patients," Br. J. Clin. Pharmacol. 22: 194-197 (1986).
5. Broly F et al, "Effect of quinidine on the dextromethorphan O-methylase activity of microsomal fractions from human liver," Br. J. Clin. Pharmacol. 28: 29-36 (1989).

6. Broly F et al, "Inhibitory studies of mexiletine and dextromethorphan oxidation in human liver microsomes," Biochem. Pharmacol. 39: 1045-1053 (1990).
7. Brosen K et al, "Extensive metabolizers of debrisoquin become poor metabolizers during quinidine treatment," Pharmacol. Toxicol. 60: 312-314 (1987)
8. Carpenter, C L et al, "Dextromethorphan and dextrorphan as calcium channel antagonists," Brain Research 439: 372-375 (1988)
9. Cavallini (1995) "Alpha-1 Blockade Pharmacotherapy in Primitive Psychogenic Premature Ejaculation Resistant to Psychotherapy," Eur. Urology 28:126-130.
10. Choi D W, "Dextrorphan and dextromethorphan attenuate glutamate neurotoxicity," Brain Res. 402: 333-336 (1987)
11. Craviso G L and Musacchio J M, "High affinity dextromethorphan binding sites in guinea pig brain," Mol. Pharmacol. 23: 619-640 (1983).
12. David J E et al., "Identification of 6',7'-Dihydroxybergamottin, a Cytochrome P450 Inhibitor, In Grapefruit Juice", Drug Metabolisms and Disposition, vol. 24, No. 12, pp. 1287-1290 (1996).
13. Dayer R et al, "Dextromethorphan O-demethylation in liver microsomes . . . " Clin. Pharmacol. Ther. 45: 34-40 (1989)
14. Feeser et al, Neurosci. Letters 86: 340-345 (1988)
15. Di Silverio et al. (1996), "Effects Compares de l'Incision Cervico-Prostatique (ICP) et de l'Association ICP et Agonistes de la LHRH dans le Traitement de l'Hypertrophie Benigne de la Prostate," Journal D'Urologie 102(3):111-116.
16. Falaschi et al. (1981), "Brain Dopamine and Premature Ejaculation: Results of Treatment with Dopamine Antagonists," Apomorphine and Other Dopaminomitics 1:117-121.
17. Feinberg (1991), "Clomipramine for Obsessive-Compulsive Disorder," AFP Clinical Pharmacology 43(5):1735-1738.
18. Ferkany et al, Eur. J. Pharmacol. 151: 151-154(1988)
19. Ferrari et al (1994), "The Selective D2 Dopamine Receptor Antagonist Eticlopride Counteracts the Ejaculatio Praecox Induced by the Selective D2 Dopamine Agonist SND 919 in the Rat," Life Sciences 55(14):1155-1162. (8 pages)
20. Fonne-Pfister et al, Biochem. Biophys. Res. Communic. 148: 1144-1150 (1987)
21. Frank H B et al., "Synthesis and Biological Evaluation of 6',7'-Dihydroxybergamottin (6,7-DHB), A Naturally Occurring Inhibitor of Cytochrome P450 3A4", Biorganic & Medicinal Chemistry Letter, vol. 7, No. 20, pp. 2593-2598, 1997.
22. Guttendorf R J et al, "Simplified phenotyping with dextromethorphan by thin-layer chromatography," Ther. Drug. Monit. 10: 490-498 (1988).
23. Hull et al. (1994), "The Roles of Nitric Oxide in Sexual Function of Male Rats," Neuropharmacology 33 (11): 1499-1504.
24. Goldstein et al., "Oral Sildenafil in the Treatment of Erectile Dysfunction," The New England Journal of Medicine, 338, pp 1397-1404 (1998).
25. Inaba T et al, "In vitro inhibition studies of two isozymes of human liver cytochrome P-450," Drug Metabolism and Disposition 13: 443-447 (1985)
26. Inaba T et al, "Quinidine: Potent inhibition of sparteine and debrisoquin oxidation in vivo," Br. J. Clin. Pharmacol. 22: 199-200 (1986)
27. Inaba T et al, "Quinidine: Potent inhibition of sparteine and debrisoquin oxidation in vivo," Br. J. Clin. Pharmacol. 22: 199-200 (1986).
28. Rashid J et al., "Quercetin, an in vitro inhibitor of CYP3A, does not contribute to the interaction between nifedipine and grapefruit juice", Br J clin Pharmac, vol. 36, pp. 460-463, 1993.
29. Jachau M R "Substrates, Specificities and Functions of the P450 Cytochromes", LIFE SCIENCES, Vol. 47, pp. 2385-2394 (1990).
30. Neal J J et al., "Inhibition of Insect Cytochromes P450 by Furanocoumarins", 1994, Pesticide Biochemistry and Physiology 50, pp. 43-50.
31. Jerzy Klinger (2000) "Vita Sexualis: The truth about human sex life", By Klinger, Pawel, Translated from Polish to English by Klinger, Jerzy, Copyright© 1994 pages 1-362.
32. Kan He et al., "Inactivation of Cytochrome P450 3A4 by Bergamottin, a Component of Grapefruit Juice", Chem. Res. Toxicol, vol. 11, pp. 252-259, 1998.
33. Katsuyuki Fukuda, et al., "Grapefruit Component Interacting with Rat and Human P450 CYP3A: Possible Involvement of Non-Flavenoid Components in Drug Interaction", Biol. Pharm. Bull., vol. 20, No. 5, pp. 560-564, May 1997.
34. Koppel C et al, "Urinary metabolism of dextromethorphan in man," Arzneim.-Forsch./Drug Research 37: 1304-1306 (1987).
35. Koyuncuoglu & Saydam, Intnl. J. Clin. Pharmacol. Ther. Tox. 28: 147-152 (1990)
36. Kupfer A et al "Dextromethorphan as a safe probe for debrisoquine hydroxylation polymorphism," Lancet ii: 517-518 (1984).
37. Leander, Epilepsy Res. 4: 28-33 (1989)
38. Bourian M et al., "Coumarin Derivatives in Grapefruit Juice and Their Interactions with Mammalian Drug Metabolising Enzyme Systems", Annual Congress on Medicinal Plant Research, vol. 44, pp. 43, 1996.
39. Obermeier M T et al., "Effects of bioflavonoids on hepatic P450 activities", Xeonbiotica, vol. 25, No. 6, pp. 575-584, 1995.
40. Marina Tinel, et al., "Inactivation of Human Liver Cytochrome P-450 by the Drug Methoxsalen and Other Psoralen Derivatives", Biochemical Pharmacology, vol. 36, No. 6, pp. 951-955, 1987.
41. Metz et al. (1997), "Premature Ejaculation: A Psychophysiological Review," Journal of Sex & Marital Therapy 23(1):3-23.
42. Musacchio J M et al, "High affinity dextromethorphan binding sites in the guinea pig brain," J. Pharmacol. Exp. Ther. 247: 424-431 (1988)
43. Napoli-Farris et al. (1984), "Stimulation of Dopamine Autoreceptors Elicits Premature Ejaculation in Rats," Pharmacology Biochemistry & Behavior 20:69-72.
44. Nielsen M D et al, "A dose-effect study of the in vivo inhibitory effect of quinidine on sparteine oxidation in man," Br. J. Clin. Pharmacol. 29: 299-304 (1990).
45. Niznik et al, Arch. Biochem. Biophys. 26: 424-432 (1990)
46. Physician's Desk Reference, 44th Edition (1988), pp. 670-671 (Medical Economics Company, 1990).
47. Prince & Feeser, Neurosci. Letters 85: 291-296 (1988).
48. Ramachander G et al, "Determination of dextrorphan in plasma and evaluation of bioavialability dextromethorphan hydrobromide in humans," J Pharm. Sci 66: 1047-1048 (1977)
49. Rodd E H, Chemistry of Carbon Compounds (Elsevier Publ., New York, 1960).

50. Steinberg G K et al, "Delayed treatment with dextromethorphan and dextrorphan reduces cerebral damage after transient focal ischemia," Neurosci Letters 89: 193-197 (1988).
51. Testa B and Jenner P, "Inhibitors Of Cytochrome P-450s and Their Mechanism of Action", DRUG METABOLISM REVIEWS, 12(1)1-117 (1981); F. P. Guengerich, "Cytochrome P450: Advances and Prospects", FASEB J., Vol. 6, pp. 667-668 (1992).
52. Tortella et al, TIPS 10: 501-507 (1989)
53. Uwe Fuhr et al., "Inhibitory effect of grapefruit juice and its bitter principal, naringenin, on CYP1A2 dependent metabolism of caffeine in man*", Br. J. Clin. Pharmacol., Department of Clinical Pharmacology, University Hospital. Frankfurt/Main, Germany, vol. 35, 1993, pp 431-436.
54. Vettican S J et al, "Phenotypic differences in dextromethorphan metabolism," Pharmaceut Res. 6: 13-19 (1989)
55. Waldinger et al. (1997), "Ejaculation-Retarding Properties of Paroxetine in Patients with Primary Premature Ejaculation: A Double-Blind, Randomized, Dose-Response Study," British Journal of Urology 79:592-595.
56. Walker E O, and Hunt V P, "An open label trial of dextromethorphan in Huntington's Disease," Clin. Neuropharmacol. 12: 322-330 (1989).
57. Chan W K et al., "Mechanism-Based Inactivation of Human Cytochrome P450 3A4 by Grapefruit Juice and Red Wine", Life Sciences, vol. 62, No. 10, pp. PL 135-142, 1998.
58. Wong B Y et al, "Dextrorphan and dextromethorphan, common antitussives, are antiepileptic and antagonize NMDA in brain slices," Neurosci Letters 85: 21-26 (1988)
59. Yingna Cai et al. "Inhibition and Inactivation of Murine Hepatic Ethoxy- and Pentoxyresorufin O-Delkylase by Naturally Occurring Coumarins", Chem. Res. Toxicol, vol. 6, pp. 872-879 (1993).
60. Brosen K, Murray M and Reidy G F, "Recent Developments In Hepatic Drug Oxidation Implications For Clinical Pharmacokinetics", CLIN. PHARMACOKINET., 18(3): 220-239, 1990.
61. Murray M and Reidy G F, "Selectivity in the Inhibition of Mammalian Cytochrome P-450 By Chemical Agents", PHARMACOLOGICAL REVIEWS, 42, 85-101 (1990).
62. Porter T D and Coon M J, "Cytochrome P-450: Multiplicity of Isoforms, Substrates, and Catalytic and Regulatory Mechanisms", J. BIOL. CHEM., Vol. 266, 13469-13472 (1991).
63. Guengerich F P, "Characterization of Human Microsomal Cytochrome P-450 Enzymes", ANNU. REV. PHARMACOL. TOXICOL. Vol, 29, pp. 241-264 (1989).
64. Martindale, The Extra Pharmacopoeia, 31st edition, pp 333 (London: The Royal Pharmaceutical Society, 1996).
65. Dayer P, Desmeules J, Collart L. Pharmacology of tramadol Drugs 1997; 53 Suppl 2:18-24.
66. Raffa R B. A novel approach to the pharmacology of analgesics. Am J Med 1996; 101(1A):40S-46S.
67. Reimann W, Hennies H H. Inhibition of spinal noradrenaline uptake in rats by the centrally acting analgesic tramadol. Biochem Pharmacol 1994; 47(12):2289-93.
68. Dayer P, Collart L, Desmeules J. The pharmacology of tramadol. Drugs 1994; 47 Suppl 1:3-7.
69. Raffa R B, Friderichs E, Reimann W, Shank R P, Codd E E, Vaught J L, Jacoby H I, Selve N. Complementary and synergistic antinociceptive interaction between the enantiomers of tramadol J Pharmacol Exp Ther 1993; 267: 331-40.
70. Lee C R, McTavish D, Sorkin E M. Tramadol. A preliminary review of its pharmacodynamic and pharmacokinetic properties, and therapeutic potential in acute and chronic pain states. Drugs 1993; 46(2):313-40.
71. Tobias J D. Seizure after overdose of tramadol. South Med J 1997; 90(8):826-7.
72. Weinbroum A A, Valery R, Gideon P, Ben-Abraham R. The role of dextromethorphan in pain control CAN J ANESTH 2000; 47: 585-596.
73. Rodd E H. Chemistry of Carbon Compounds, Elsevier Publ, New York, 1960.
74. Grond S, Thomas M, Detlev Z et al. "Analgesic efficacy and safety of tramadol enantiomers in comparison with the racemate: a randomised, double-blind study with gynaecological patients using intravenous patient-controlled analgesia" Pain 1995; 62(3):313-320.
75. Shipton E A. "Reviews: Tramadol—Present and Future" Anaesth Intensive Care 2000; 28:363-374.
76. Barnung S K, Treschow M, Borgbjerg F M. "Respiratory depression following oral tramadol in a patient with impaired renal function" Pain 1997; 71:111-112.
77. Wiebalck A et al. "Sind Tramadol-Enantiomere für die postoperative Schmerztherapie besser geeignet als das Racemat? Eine randomisierte, Plazebo- und Morphin-kontrollierte Doppelblindstudie", Der Anaesthesist, 1998; 47: 387-394.
78. Lintz et al., Arzneim.-Forsch./Drug Res. 1981; 31(11), 1932-1943.
79. Rajfer J, Aronson W J, Bush P A, Dorey F J, Ignarro L J. Nitric oxide as a mediator of relaxation of the corpus cavernosum in response to nonadrenergic, noncholinergic neurotransmission. N. Eng. S. Med. 1992; 326: 90-4.
80. Andersson K E, Wagner G. Physiology of the penile erection. Physiol. Rev. 1995; 75: 191-236.
81. Burnett A L. The role of nitric oxide in the physiology of an erection. Biol. Reprod. 1995; 52: 485-9.
82. Boolell M, Allen M J, Ballard S A, Gepi-Attee S, Muirhead G J, Naylor A M, Osterloh I H, Gingell J C. Sildenafil: an orally active type 5 GMP-specific phosphodiesterase inhibitor of penile erection dysfunction. Int. J. Impot. Res. 1996; 8: 47-52.
83. Daly J W, Fredholm B B. Caffeine: an atypical drug of dependence. *Drug Alcohol Depend.* 1998; 51:199-206.
84. Nehlig A, Daval J-L, Denry G. Caffeine and the central nervous system: mechanisms of action, biochemical, metabolic and psychostimulant effects. *Brain Res Brain Res Rev.* 1992; 17:139-170.
85. Fredholm B B, Bättig K, Holmèn J, et al. Actions of caffeine in the brain with special reference to factors that contribute to its widespread use. *Pharmacol Rev.* 1999; 51:83-133.
86. Ongini E, Fredholm B B. Pharmacology of adenosine $A_{2A}$ receptors. *Trends Pharmacol Sci.* 1996; 17:364-372.
87. Klotz K-N, Hessling J, Hegler J, et al. Comparative pharmacology of human adenosine receptor subtypes: characterization of stably transfected receptors in CHO cells. *Naunyn Schmiedebergs Arch Pharmacol.* 1998; 357:1-9.
88. Fredholm B B. Adenosine, adenosine receptors and the actions of caffeine. *Pharmacol Toxicol.* 1995; 76:93-101.
89. Sawynok J. Pharmacological rationale for the clinical use of caffeine. *Drugs.* 1995; 49:37-50.
90. Grobbee D E, Rimm E B, Giovannucci E, et al. Coffee, caffeine, and cardiovascular disease in men. *N Engl J Med.* 1990; 323:1026-1032.
91. Jee S H, He J, Whelton P K, et al. The effect of chronic coffee drinking on blood pressure: a meta-analysis of controlled clinical trials. *Hypertension.* 1999; 33:647-652.

92. Bättig K and Welzl H (1993) Psychopharmacological profile of caffeine, in *Caffeine, Coffee and Health* (Garattini S ed) pp 213-253, Raven Press, New York.
93. Ledent C, Vaugeois J M, Schiffmann S N, Pedrazzini T, Elyacoubi M, Vanderhaeghen J J, Costentin J, Heath J K, Vassart G and Parmentier M (1997) Aggressiveness, hypoalgesia and high blood pressure in mice lacking the adenosine A2A receptor. *Nature* 388: 674-678.
94. Myers D E, Shaikh Z and Zullo T G (1997) Hypoalgesic effect of caffeine in experimental ischemic muscle contraction pain. Headache 37: 654-658.
95. Lieberman H R, Wurtman R J, Emde G G and Coviella I L (1987) The effects of caffeine and aspirin on mood and performance. *J Clin Psychopharmacol* 7: 315-320.
96. Ward N, Whitney C, Avery D and Dunner D (1991) The analgesic effects of caffeine in headache. *Pain* 44: 151-155.
97. Migliardi J R, Armellino J J, Friedman M, Gillings D B and Beaver W T (1994) Caffeine as an analgesic adjuvant in tension headache. *Clin Pharmacol Ther* 56: 576-586.
98. Ghelardini C, Galeotti N and Bartolini A (1997) Caffeine induces central cholinergic analgesia. *Naunyn-Schmiedebergs Arch Pharmacol* 356: 590-595.
99. Carter A J, O'Connor W T, Carter M J and Ungerstedt U (1995) Caffeine enhances acetylcholine release in the hippocampus in vivo by a selective interaction with adenosine A1 receptors. *J Pharmacol Exp Ther* 273: 637-642.
100. Rainnie D G, Grunze H C, McCarley R W and Greene R W (1994) Adenosine inhibition of mesopontine cholinergic neurons: Implications for EEG arousal. *Science* 263: 689-692.
101. Snel J (1993) Coffee and caffeine: Sleep and wakefulness, in *Coffee, Caffeine and Health* (Garattini S ed) pp 255-290, Raven Press, New York.

The invention claimed is:

1. A method of effectively treating premature ejaculation in a patient, comprising administering to the patient in need of such treatment an amount of agents comprising a) dextromethorphan or a pharmaceutically acceptable salt thereof, b) tramadol or a pharmaceutically acceptable salt thereof, and c) sildenafil or a pharmaceutically acceptable salt thereof, whereby the combined amount of said agents is effective to treat the premature ejaculation in the patient.

2. The method of claim 1, wherein the agents are administered separately.

3. The method of claim 1, wherein the agents are administered in combination.

4. The method of claim 1, wherein the agents are administered prior to sexual activity.

5. The method of claim 1, wherein the agents are administered orally, by means of an implant, parenterally, sub-dermally, sublingually, rectally, topically, or via inhalation.

6. The method of claim 5, wherein the agents are administered orally.

7. The method of claim 1 wherein the agents are administered in a dosage form selected from the group consisting of a tablet, a multiparticulate formulation for oral administration; a solution, a sustained release formulation, a suspension or elixir for oral administration, an injectable formulation, an implantable device, a topical preparation, a transdermal delivery device, a suppository, a buccal tablet, and an inhalation formulation.

8. The method of claim 7, wherein the dosage form is further defined as a solid oral dosage form formulated as a tablet or capsule.

9. The method of claim 1, wherein the ratio of dextromethorphan to tramadol is from about 15:1 to 1:15.

10. The method of claim 9, wherein the ratio of dextromethorphan to tramadol is from about 10:1 to 1:10.

11. The method of claim 10, wherein the ratio of dextromethorphan to tramadol is from about 5:1 to 1:5.

12. The method of claim 11, wherein the ratio of dextromethorphan to tramadol is about 1:2.

13. The method of claim 1, wherein caffeine is included as an agent.

14. A pharmaceutical composition comprising a therapeutically effective amount of a combination of agents, the combination comprising a) dextromethorphan or a pharmaceutically acceptable salt thereof, b) tramadol or a pharmaceutically acceptable salt thereof, and c) sildenafil or a pharmaceutically acceptable salt thereof.

15. The pharmaceutical composition of claim 14, wherein the pharmaceutical composition further comprises caffeine.

* * * * *

UNITED STATES PATENT AND TRADEMARK OFFICE
CERTIFICATE OF CORRECTION

PATENT NO.        : 8,604,082 B2                                          Page 1 of 1
APPLICATION NO. : 12/097157
DATED             : December 10, 2013
INVENTOR(S)       : Chandra U. Singh It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1029 days.

Signed and Sealed this
Twenty-second Day of September, 2015

Michelle K. Lee
*Director of the United States Patent and Trademark Office*